US005565633A

United States Patent [19]

Wernicke

[11] Patent Number: 5,565,633
[45] Date of Patent: Oct. 15, 1996

[54] SPIRAL TRACTOR APPARATUS AND METHOD

[76] Inventor: Timothy K. Wernicke, 912 Summertree La., Southlake, Tex. 76092

[21] Appl. No.: 535,921

[22] Filed: Sep. 28, 1995

Related U.S. Application Data

[63] Continuation-in-part of Ser. No. 100,468, Jul. 30, 1993, Pat. No. 5,454,276.

[51] Int. Cl.$^6$ .......................... G01N 29/04; G01N 29/26; G01M 19/00
[52] U.S. Cl. .......................... 73/865.8; 73/866.5; 73/623; 324/220; 324/228
[58] Field of Search .............. 73/865.8, 866.5, 73/623, 40.5 R; 324/220, 226, 228

[56] References Cited

U.S. PATENT DOCUMENTS

| | | | |
|---|---|---|---|
| 3,238,448 | 3/1966 | Wood et al. | 324/37 |
| 3,483,466 | 12/1969 | Crouch et al. | 324/220 |
| 3,593,122 | 7/1971 | Barton et al. | 324/220 |
| 3,786,684 | 1/1974 | Wiers et al. | 324/220 |
| 3,810,384 | 5/1974 | Evans | 73/626 |
| 3,906,357 | 9/1975 | Runshang | 324/37 |
| 3,906,358 | 9/1975 | Stone | 324/220 |
| 4,072,894 | 2/1978 | Barton | 324/221 |
| 4,105,972 | 8/1978 | Smith | 324/220 |
| 4,107,605 | 8/1978 | Hudgell | 324/220 |
| 4,170,902 | 10/1979 | Pallan | 73/866.5 |
| 4,244,296 | 1/1981 | Vertut | 73/40.5 R X |
| 4,310,796 | 1/1982 | Braithwaite et al. | 324/220 |
| 4,361,044 | 11/1982 | Kupperman et al. | 73/623 |
| 4,370,895 | 2/1983 | Wright | 74/216 |
| 4,439,730 | 3/1984 | Kauffman | 324/232 |
| 4,444,777 | 5/1984 | Sharp et al. | 324/220 |
| 4,458,601 | 7/1984 | Braithwaite et al. | 104/138 G |
| 4,628,613 | 12/1986 | Laymon | 33/544 |
| 4,742,298 | 5/1988 | Ando et al. | 324/220 |
| 4,769,598 | 9/1988 | Krieg et al. | 324/226 |
| 4,789,827 | 12/1988 | Bergander | 324/220 |
| 4,851,773 | 7/1989 | Rothstein | 324/220 |
| 4,952,875 | 8/1990 | Adams et al. | 324/220 |
| 5,068,608 | 11/1991 | Clark, Jr. | 324/220 |
| 5,134,367 | 7/1992 | Griffith et al. | 324/220 |

FOREIGN PATENT DOCUMENTS

| | | | |
|---|---|---|---|
| 108489 | 9/1978 | Japan | 73/623 |
| 43563 | 2/1987 | Japan | 324/220 |
| 58158 | 3/1988 | Japan | . |
| 218953 | 8/1990 | Japan | 324/220 |
| 550573 | 4/1977 | U.S.S.R. | . |
| 1283640 | 1/1987 | U.S.S.R. | 324/220 |

*Primary Examiner*—Hezron E. Williams
*Assistant Examiner*—Daniel S. Larkin
*Attorney, Agent, or Firm*—John W. Montgomery; Ross, Clapp, Korn & Montgomery, L.L.P.

[57] ABSTRACT

A spiral pig apparatus is provided for axial movement through a pipe of the type having a cylindrical interior surface defining a central axis. The spiral pig apparatus includes a first and a second section coupled to each other for axial movement of both sections and for relative rotation between the first and second sections. A first plurality of wheels is attached to the first section. Each of the first plurality of wheels is attached at a first rolling angle, relative to the pipe axis for rolling contact with the interior surface of the pipe, and for supporting the first section spaced inward from the interior surface of the pipe. A second plurality of wheels is attached to the second section. Each of the second plurality of wheels is attached at a second rolling angle, relative to the pipe axis for rolling contact with the interior surface of the pipe. The second rolling angle is different from the first rolling angle of the first set of wheels. The second plurality of wheels is also attached for supporting the second section spaced inward from the interior surface of the pipe. A drive mechanism is operatively connected to the spiral pig for causing the pig to move through the pipe, as the first and second sections rotate relative to each other.

17 Claims, 10 Drawing Sheets

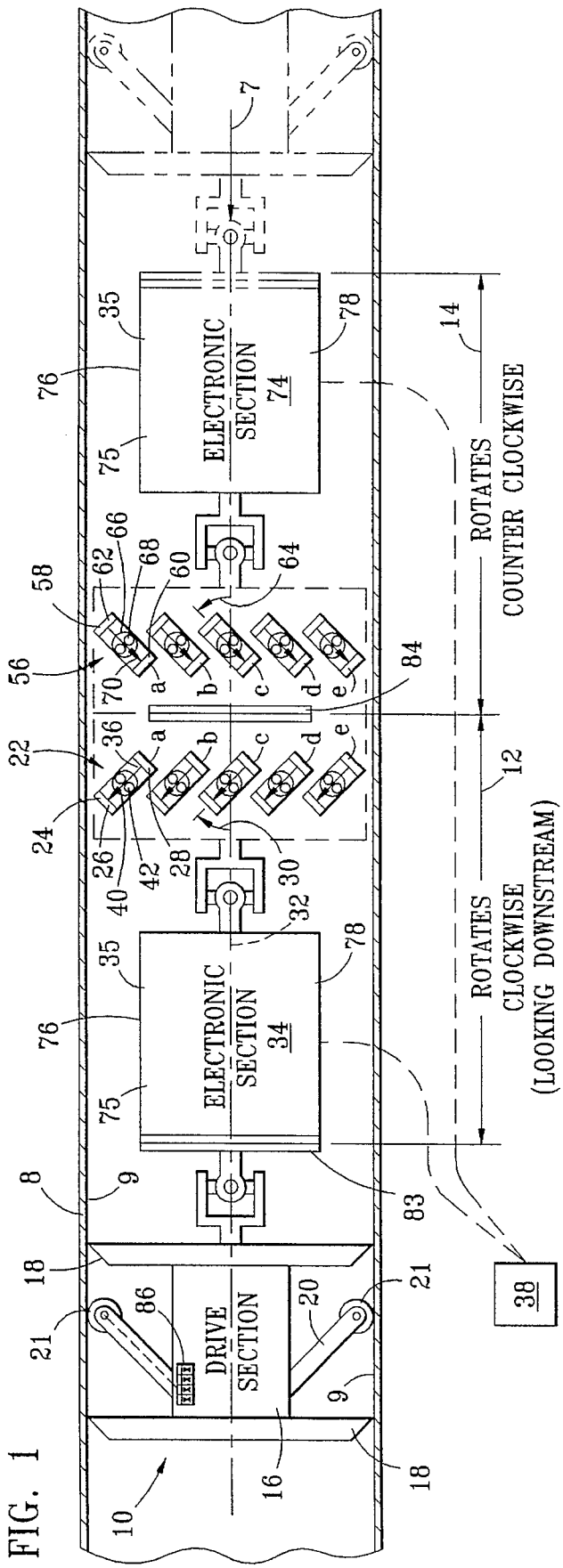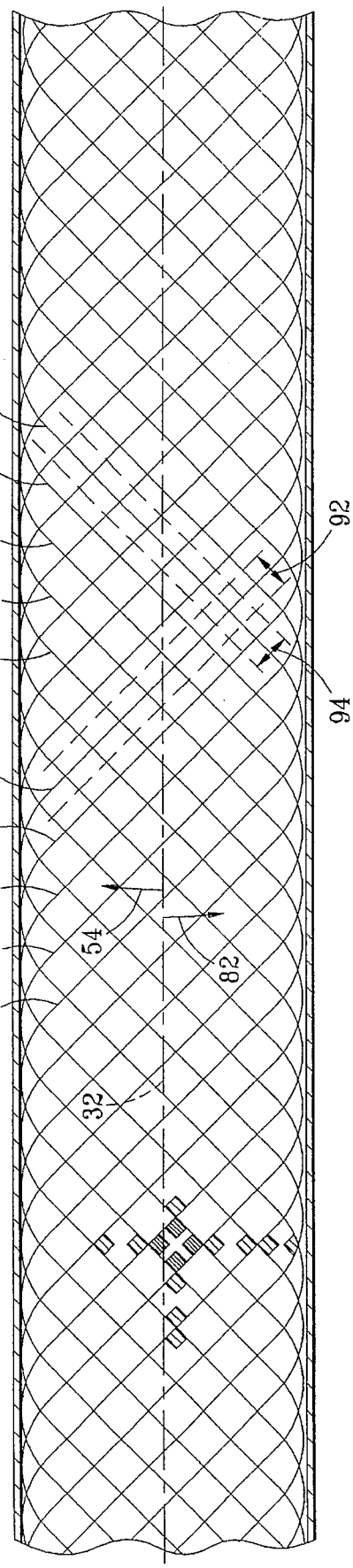

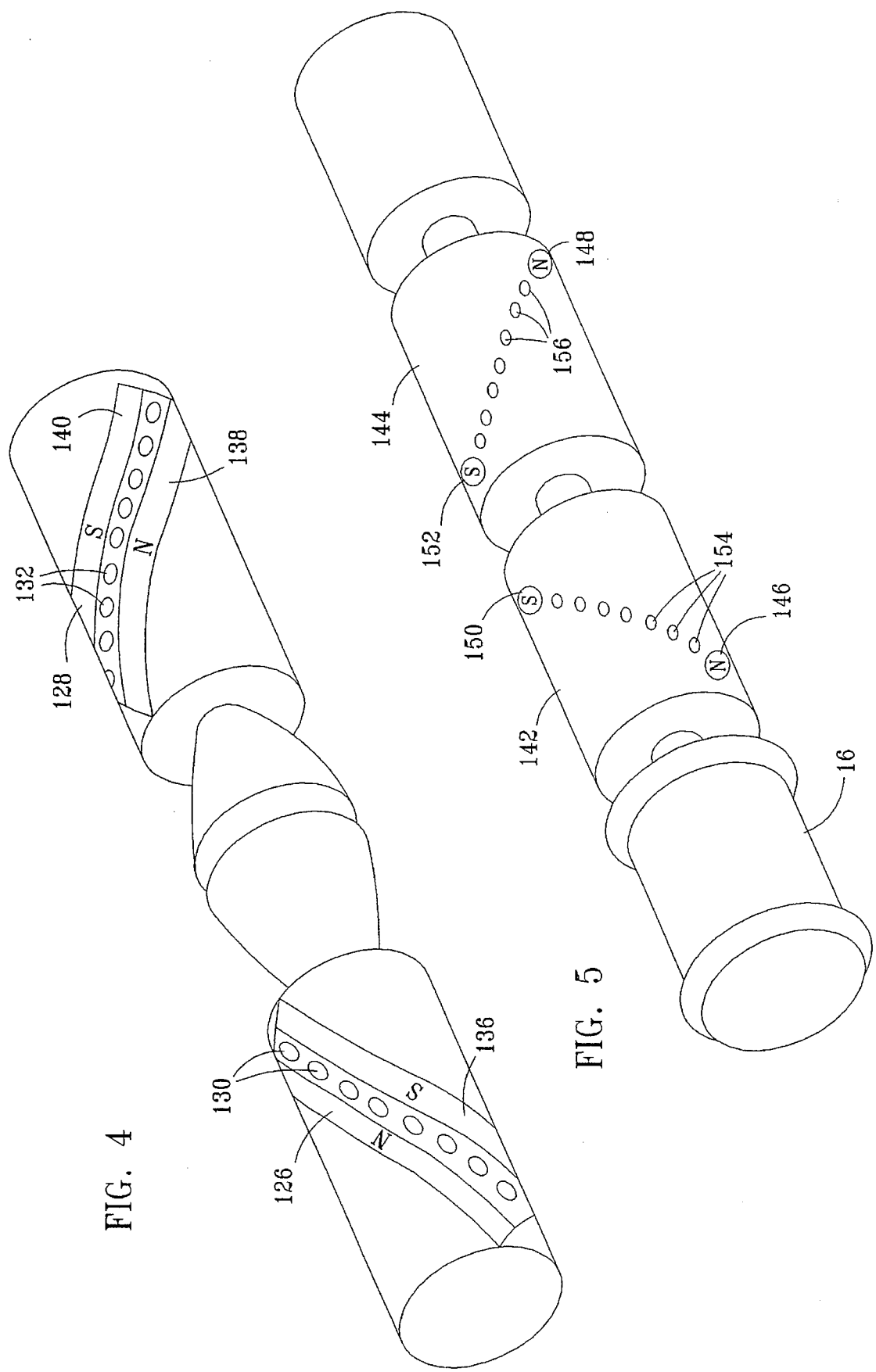

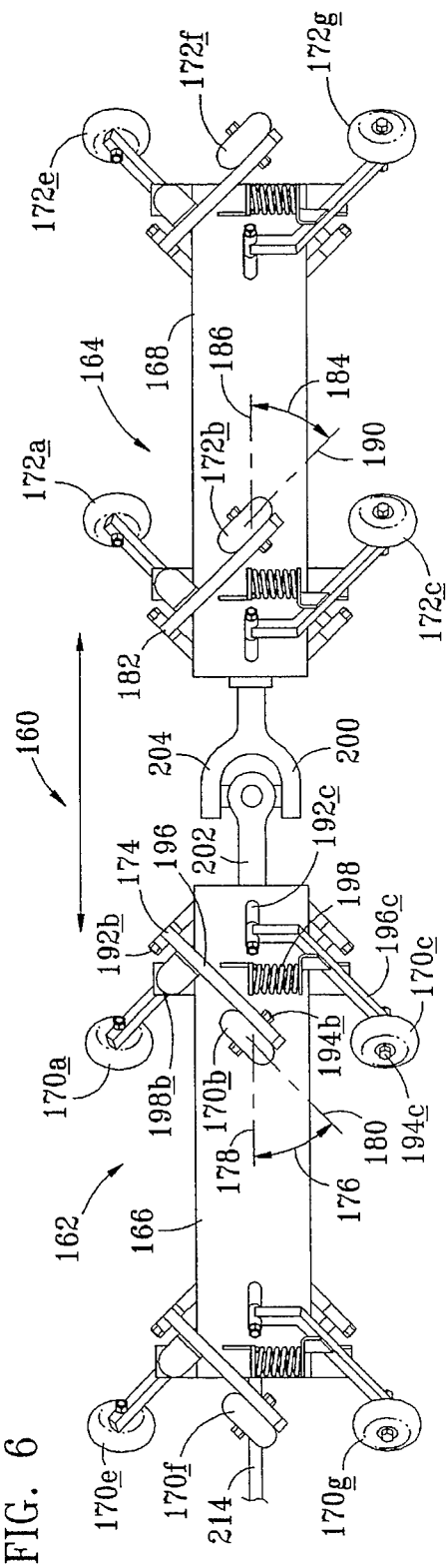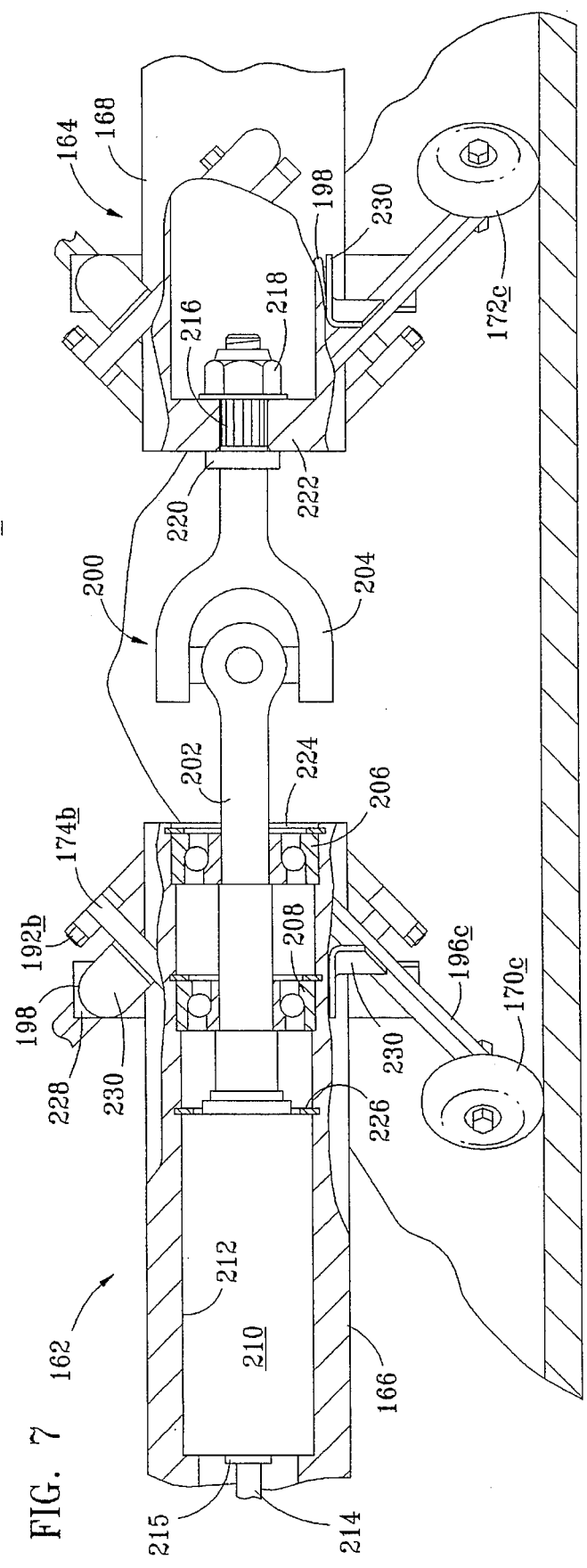
FIG. 6
FIG. 7

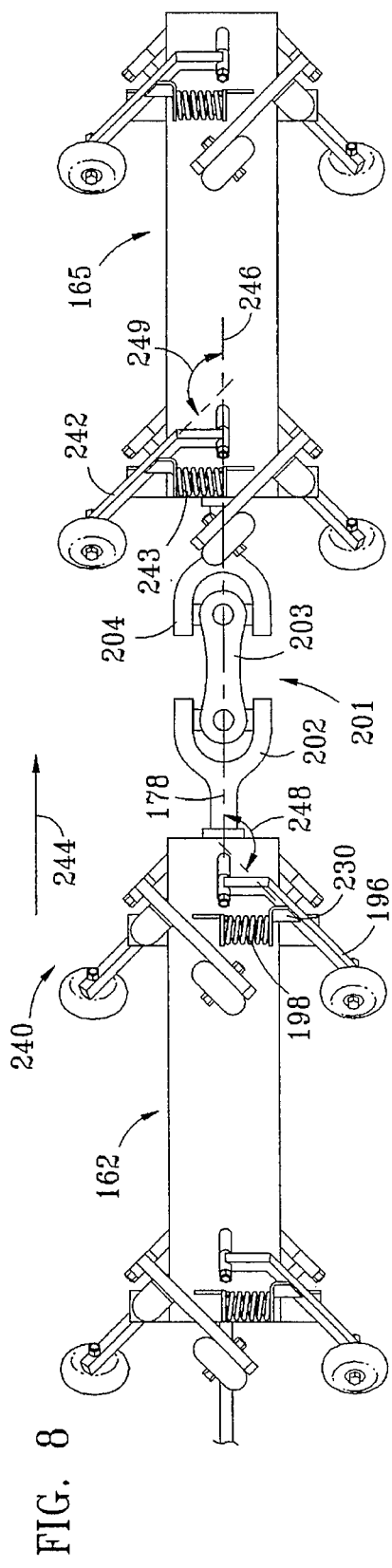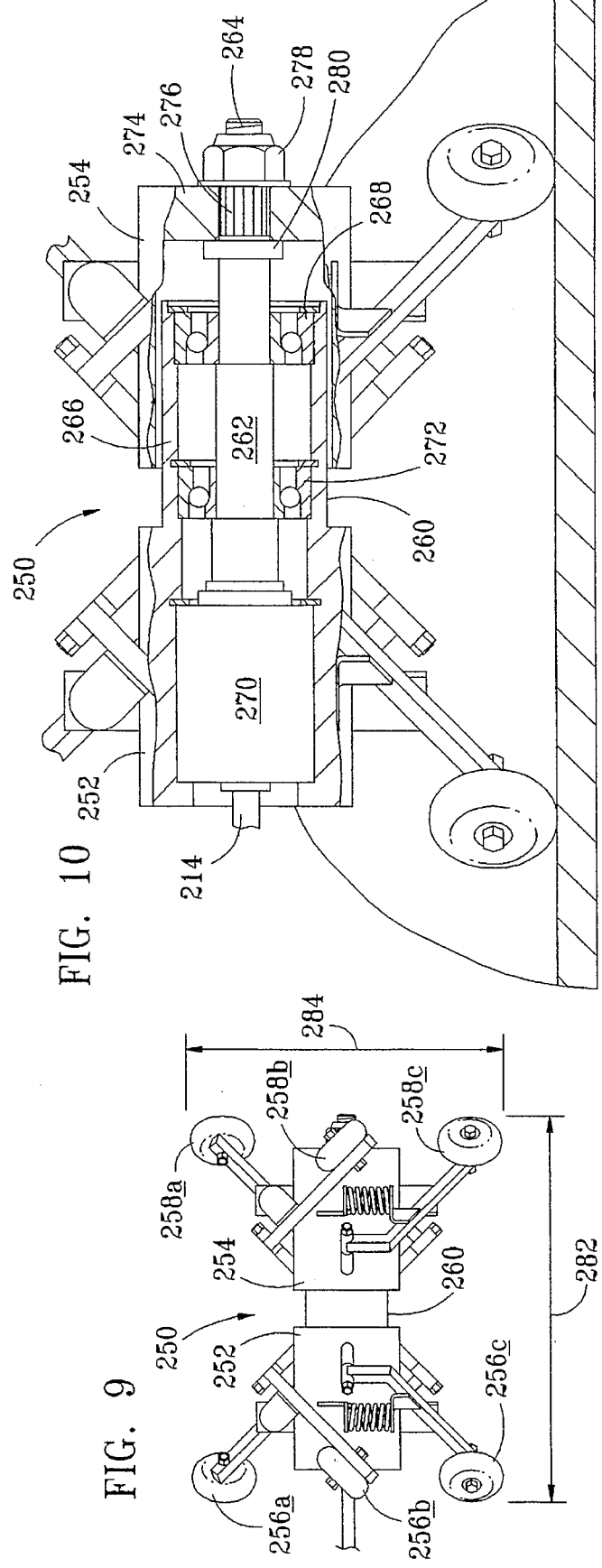

SPIRAL TRACTOR APPARATUS AND METHOD

CROSS-REFERENCE TO RELATED APPLICATIONS

This application is a continuation-in-part application of U.S. Patent Application, entitled "MULTI-DIRECTIONAL MAGNETIC FLUX PIPE INSPECTION APPARATUS AND METHOD", which was filed on Jul. 30, 1993, assigned Ser. No. 08/100,468 and to be issued on Oct. 3, 1995 as U.S. Pat. No. 5,454,276.

TECHNICAL FIELD OF THE INVENTION

The present invention relates to an apparatus and method for moving devices through the inside of a pipe, and particularly, to a tractor pig apparatus and method of operation for moving the pig, and, more particularly, for moving other devices attached to the pig, through an existing pipe or pipeline.

BACKGROUND OF THE INVENTION

Numerous pigs, including pipe inspection pigs are in existence and have been used in connection with moving various devices through pipe, including pipeline-cleaning devices and non-destructive inspection of pipelines for gaseous or liquid materials, such as natural gas, liquid hydrocarbons, or water.

Much of the existing underground and undersea pipelines are made out of ferromagnetic steel and for that reason, inspection devices such as eddy current detectors, as may be used in inspection of non-ferromagnetic tubing, such as stainless steel or other types of tubing used in heat exchangers and the like are not particularly useful in connection with underground steel pipelines, such as chemical pipelines, liquid hydrocarbon pipelines, gas pipelines, water or sewage pipes, and the like.

Various methods of detecting flaws or defects from the inside of a pipe or pipeline have been attempted with varying degrees of success. Ferromagnetic induction devices have been used as disclosed in U.S. Pat. No 4,742,298. This invention was directed to determining the presence and the magnitude of surface flaws and to overcoming difficulties encountered in determining the presence and the magnitude of surface flaws in a pipe. The solution proposed was to use a cylindrical primary alternating current coil which is coaxially aligned with the pipe to generate a high frequency AC magnetic field in the pipeline. A multiple cylindrical secondary AC sensing coil was arranged at prescribed intervals in a circumferential direction around the interior of the pipe, each secondary coil having an axis parallel to the axis of the primary coil. The AC voltage sensed at each secondary coil was set to be proportional to the density of a parallel component of magnetic flux caused by the AC magnetic field generator.

Eddy current sensing probes have also been used primarily in connection with non-destructive inspection and testing of relatively thin-walled tubing which was not ferromagnetic material. Such tubing does exist in steam generators and heat exchangers, which have been the primary focus of eddy current probes, such as a single direction rotating head profilometer, as disclosed in U.S. Pat. No. 4,851,773. One embodiment of that device discloses an electromechanical eddy current probe having a rotatable sensing head for sensing the wall thickness and for locating local defects in a tube or conduit. Basically, the mechanical profilometer probe was designed to detect dents in the interior surface of steam generator tubes. The position of the rotating head was varied along the length of the tubing being inspected as the probe was drawn through the tubing with a cable.

Another eddy current probe is disclosed in U.S. Pat. No 4,952,875 in which a plurality of pairs of diametrically opposed sensing coils are shown alternatingly staggered along the longitudinal axis of the test sensor to give complete coverage of the interior pipe surface. Such sensors were further permitted to move in and out to accommodate the size differences or constrictions in the pipeline. However, the sensor probe was intended to move longitudinally through the pipeline.

Also, U.S. Pat. No 5,068,608 discloses multiple coil eddy current probe system and an eddy current probe is disclosed in which a defect was first detected when the probe was positioned adjacent the defect and a series of axially spaced probes were activated to sense and detect the extremities of a crack or other discontinuity. Generally, eddy current probes have not been particularly successful with respect to underground pipelines constructed of steel or other ferromagnetic materials and having pipeline walls with thicknesses substantially greater than the normal eddy current penetration depth. However, one attempt to provide an eddy current probe or ferromagnetic pipeline flaw detection was disclosed in U.S. Pat. No. 4,107,605. There was no indication of the usefulness of such probes in connection with determining longitudinal cracks which were parallel to the direction of movement of the probe assembly.

Popular and useful sensors for ferromagnetic pipeline inspection have been magnetic flux generators and magnetic flux leakage sensors which were positioned circumferentially around an inspection pig which were moved longitudinally through the pipeline. Examples of such sensors were disclosed in U.S. Pat. Nos. 4,105,972, 4,310,796, 4,444,777 and 4,458,601. The operation of such magnetic flux detection probes was described in U.S. Pat. No 4,789,827 in connection with a magnetic flux detection probe in which the sensors were shown intentionally spaced at different radial distances, or spaced different distances from the interior pipe surface, in an effort to obtain greater accuracy with respect to the location of the flaw or defect on the inside or the outside of the pipe wall.

Some attempts have been made to detect defects at different angular orientations in connection with testing and inspecting pipes as they were being manufactured. U.S. Pat. No 3,906,357 disclosed an exterior pipe testing device in which there were two external sensor sections, one having a plurality of fixed sensing shoes circumferentially spaced around the pipe to be inspected which depended upon linear movement of the pipe therethrough for detecting flaws or defects primarily oriented circumferentially around the pipe. A second inspection unit was provided with a pair of opposed magnetic sensing shoes which are rotated rapidly around the outside of the pipe to be inspected in an effort to detect longitudinal cracks which might have otherwise gone unnoticed with the fixed shoe sensing unit. Complex circuitry was used to coordinate the sensor input from each of the sensing units with a rotating magnetic pulse generator geared to the linear motion of the pipe being manufactured. A purpose of this device was to actuate one or more spray cans at the linear and the circumferential position where a manufacturing flaw was detected either by the linear inspection unit or the rotary inspection unit. Application of such a testing device to on-site underground pipelines has not been demonstrated.

Another exterior pipe testing device has been disclosed in U.S. Pat. No 4,439,730, in which pairs of north and south poles of magnets were held adjacent to the exterior wall of a pipe at uniformly spaced apart positions circumferentially around the pipe. The north and south poles were positioned between the north and south poles of longitudinally spaced apart circular magnets around the pipe. The circumferential spaced apart magnets were rotated at a high rate of speed so that orthogonically directed resultant magnetic fields were produced on opposite sides of the pipe between the north and south pole of the rotating magnets. Pairs of flux detectors were interposed on opposite sides of the rotating magnet. The magnets were rotated at a sufficiently high rate of speed relative to the longitudinal motion of the pipe since the flux field interruptions in the same incremental area of the pipe. Again, complex circuitry was required in order to coordinate the sensor input from each of the sensing units because of the high rotational speed (320 revolutions per minute in the example set forth in '730) in order to keep track of the sampled signals from the two overlapping sensors and further, to coordinate them to a longitudinal position along the pipe. At a longitudinal traveling speed of 80 feet per minute as set forth in the example, the device had to make four complete revolutions during every one foot of travel, which was consistent with the sensor field slightly over three inches long, so that 100% of the pipe surface could be covered. Such a device is not considered practical for internal inspection of existing underground pipelines. Potentially, the rate of rotation may not be achievable for internal pipe inspection devices.

Pipeline flaw detectors for use inside of existing pipelines have also provided rotary mechanisms for rotating sensing shoes helically through the pipeline as the detector was moved linearly therealong. One such device was disclosed in U.S. Pat. No. 3,238,448 which, upon detecting a flaw, actuated a strong electromagnet to magnetize the corresponding portion of the pipeline so that the position of the defect could be detected from aboveground with magnetic sensors. This device rotated two opposed search units in a single direction such that only very large flaws could be accurately detected and locating any such detected flaws was dependent upon a second careful searching action for the magnetized pipe section from aboveground.

Another pipeline inspection apparatus was disclosed in U.S. Pat. No 4,072,894 which produces a circumferentially directed magnetic flux field as flux leakage detection sensors were resiliently held against the pipe wall surface and helically moved through the pipe to pass transversely across any longitudinally extending anomalies in the pipe wall. This device produced only a circumferentially directed magnetic flux and produced helical movement of the sensing probes in only one direction.

Another popular and widely used internal magnetic flux gas pipe inspection devices comprised a pipeline pig which had sealing cups around the exterior perimeter to both center the apparatus and to drive it by differential gas pressure along the pipeline. A magnetic flux was generated by multiple circumferentially spaced magnets with north and south poles axially spaced apart and a magnetic flux sensor interposed therebetween. In operation, the pig traveled linearly through the pipeline and sensory input data from each sensor was recorded as a function of distance of travel. When a defect, void, or other anomaly in the pipe was indicated by sensing an interruption of a smooth longitudinal magnetic flux, then such an anomaly was recorded on a graph as a function of time or distance. A major drawback of this device was that the longitudinal, or axially aligned, magnetic flux could not always detect longitudinal voids or defects such as a uniform deterioration along a continuous welded seam of the pipeline. Resolution was determined by the size of the multiple sensor unit. A second set of circumferentially positioned magnetic flux generators and flux leakage sensors could be positioned at a small staggered distance with respect to the first set so that the space between the flux generator and sensor shoes was covered by the second set of sensors. Still, minor disturbances at the start of a longitudinal defect and at a distant end of the longitudinal defect could go unnoticed on a graph.

The best resolution available was approximately limited by the size of the gap between the sensors. Often, one or more of the multiple sensors could fail during a run several miles through a pipeline, which could give an entire line of approximately one to three inches wide in which no discontinuities would be detected along the length of the pipe. In order to reduce some of this risk, the pigs were often rotated at up to about a 1° angle, which amounted to about one revolution per 1,000 linear feet. The magnetic flux was still linearly aligned in the axial direction and the small amount of rotation, if any, was so small that longitudinal voids continue to be substantially undetectable.

Pigs for electronic or for magnetic inspection, as well as pigs for other purposes, such as x-ray inspection, visual inspection, welding, coating and cleaning, have also suffered from deficiencies in the modes of propelling both the pig and the useful devices attached to the pig, through the inside of a pipe. Pigs have been propelled by pipeline flow, but this has not always been adequate. For example, pressure or flow propulsion has not been adequate for empty pipes or for severely leaking pipes.

Inspection pigs have sometimes been propelled with spring-loaded drive wheels, rollingly held against the pipe wall. Spring-loaded idler wheels provided opposed force to hold drive wheels against the pipe. All of the wheels were aligned for rolling parallel to the pipe axis. The traction of the drive wheel in any sludge, which usually accumulated at the bottom of the pipe, was sometimes inadequate.

Some pigs have been drawn through pipe with cables and winches, but this has not been acceptable over very long distances, especially where bends exist in pipeline along the intended path of the pig. The use of cable pulling has required substantial anchoring of the winches. In cases of above-ground pipes, as with pipeline stored in sections, special anchoring of the pipe relative to the winches has also been required.

SUMMARY OF THE INVENTION

The current invention overcomes the problems of the prior art by providing a pig with a plurality of sets of wheels for rolling contact with the interior of the pipe and for supporting the pig therein, and including a source of motivating power by which the pig sections are moved through the pipe interior, so that at least two sections rotate relative to each other as the pig moves through the pipe.

In one embodiment, the pig is provided with two flux generator and sensor sections, which sections are counter-rotated as they are moved through the pipeline. The two sections each have one or more flux generators correspondingly interposed with one or more sensors, which flux generators and interposed sensors are angularly oriented to a helical angle caused by simultaneous linear and rotational movement of the sections through the pipeline. Preferably, the two sections of generators and sensors are counter-rotated at opposite angles with equal magnitude. For example, one section rotates at +θ° and one at −θ° where θ° is a constant or fixed helical angle. Thus, the two separate sections spiral in counter-rotational directions uniformly through the pipeline. The angle θ° is selected to allow the pig to move rapidly through the pipeline with substantially complete coverage from both angularly disposed sensor sections. Uniquely, the sensory data from each of the flux generators and sensors can detect discontinuities both longitudinally and circumferentially in the pipe. To increase the sensitivity, a plurality of sensors are used in each section, each sensor positioned circumferentially around each section of the pig so that the entire surface of the pipeline is scanned by at least one sensor of each section as the pig moves through the pipeline. The sensory data from each sensor in one section is coordinated to sensory data from a corresponding sensor in the other section depending on the fixed relative rotation angle. Superimposing the data from all of the sensors for both of the sections produces a grid pattern which is useful to confirm and further define circumferential deterioration, defects, or anomalies as well as longitudinal deterioration, defects, or anomalies. An odometer reading, a graphical time indicator, a direct distance measurements, or another distance indicating mechanism may be superimposed on the grid pattern to confirm synchronization of the grid pattern to accurately specify where any detected feature, defect, deterioration, flaw, or anomaly is physically located along the length of the pipeline. Circumferential positioning of any detected feature around the pipeline is also determinable based upon the relative circumferential location of the particular sensors providing the input data so that cost-effective repairs can be made. Preferably, the sensors are rotated and also the flux is generated at the same helical angle. Advantageously, opposite angles for the two counter-rotating flux generating and sensing units will produce a uniform set of graphs for overlapping depiction of the sensor data, thereby substantially increasing the resolution of the graphical depiction obtained. The data may be recorded separately and later superimposed using computer analysis techniques. Alternatively, an on-board processor computer may simultaneously combine the signals from the two flux generator and sensor units. The input from the odometer may also be combined with the flux generator signals on board.

According to one feature of a preferred embodiment, the rotation of each of the flux generating and sensor units is synchronized with or timed to each other so that precision counter-rotation is accomplished. Both sensor sections may be synchronized to a linear odometer. Alternatively and advantageously, the sections are directly geared to each other to insure synchronization.

A further advantage is provided by the capability of a counter-rotating inspection pig according to one aspect of the present inventive device to locate longitudinal pipe seams and lack of homogeneity in the pipeline material. If the seams are found to be aligned in a position corresponding to a particular accelerated corrosion mechanism, then adverse effects on the pipeline might be expected and repair schedules can be correspondingly adjusted. Thus, the repair and/or replacement schedule can be more accurately determined where seam positions are accurately detected during inspection. This is true even where no other flaws, pits, defects, or other anomalies are detected. Alternating seam positions in adjacent pipe section is typical in modern pipelines. Aligned seams could lead to catastrophic failure, such as a propagated eruption along an extended length of pipeline. Thus, detection of faulty installation is important.

Also, alignment of the longitudinal seam of any pipe section with a primary or secondary failure mechanism is an important aspect to detect. Applicant's invention provides these capabilities in a fast-moving internal pipe inspection pig.

Another aspect of the invention is the use of a spiral tractor apparatus to move devices for inspection, such as the multi-directional magnetic flux pipe inspection apparatus, other magnetic, electronic, x-ray or visual inspection devices, pipe cleaning devices, pipe construction or weld clamping devices, internal coating, lining or other repair devices and similar devices heretofore pulled by cable or carried by traditional straight line driven internal pipe devices.

According to one aspect of the invention, a spiral apparatus is provided for axial movement through a pipe of the type having a cylindrical interior surface, defining a central axis. The spiral apparatus includes a first section and a second section coupled to the first section for axial movement therewith and for relative rotation with respect to the first section. The first plurality of wheels is attached to the first section, each of the first plurality of wheels is attached at a first rolling angle relative to the type axis for rolling contact with the interior surface of the pipe and for supporting the first section spaced inward from the interior surface of the pipe. A second plurality of wheels is attached to the second section. Each of the second plurality of wheels is attached at a second rolling angle relative to the pipe axis for rolling contact with the interior surface of the pipe and for supporting the second section, spaced inward from the interior surface of the pipe. The first and second rolling angles are different from each other and are predetermined such that the first section and the second section rotate relative to each other as the sections move axially through the pipe. A power source is operatively connected to the spiral pig for causing the pig to move through the pipe as the first and second sections rotate relative to each other, with the respective first and second plurality of wheels rollingly engaged on the interior surface of the pipe.

According to another aspect of the invention, wheels of the first section are at a different rolling contact angle from the wheels of the second section. Each power source includes an onboard motor coupled between the first and second sections of the pig, receiving energy from an external power supply, such as a remote power source connected as through an electrical cable, a hydraulic hose or a pneumatic hose, which is drawn into the pipe with the pig. The motor is operatively coupled for rotating the sections relative to each other, so that the relative rolling contact angles between the first section and the second section causes at least one of the pigs to spiral through the pipeline, thereby providing axial movement to the pig.

According to one aspect of the invention, the motivating power is provided by a motor and power supply on board a first section, such as a battery and D.C. electrical motor, coupled to a second section, for providing relative rotation between the sections and with angularly disposed wheels on at least one of the sections, so that relative rotation between the sections causes the at least one section to spiral through the pipe at a helical angle corresponding to the angle of the wheels with respect to the pipe axis and so that the pig is moved axially through the pipe as the at least one section rotates relative to the other section.

According to another aspect of the invention, the first and second sections have wheels attached thereto at substantially inverse rolling contact angles, so that each section counter-rotates with respect to the other at a substantially equal rate as the pig moves axially through the pipeline.

According to another aspect of the invention, each section of the pig is coupled to the other with a rigid shaft for relative rotation, and each section is provided with a single set of wheels aligned circumferentially and equally spaced therearound, so that the total linear distance between the points of contact between the separate sets of wheels is approximately equal to, or greater than, one times the diameter of the pipe for best bend traversing, or one and one-half times as a balance between bendability and tumbling prevention, so that the pig can move through the pipe with counter-rotation between the sections while avoiding unwanted tipping or tumbling as might tend to result from a pig having a length approximately equal to, or less than, the pipe diameter.

According to another alternative embodiment of the invention, each section has sets of spaced-apart wheels, each set circumferentially aligned and radially spaced to support the section centralized within the pipe, and each section having a length approximately one and one-half times the pipe diameter, with the sections coupled for relative rotation through a universal joint or other flexible coupling mechanism by which the units may rotate relative to each other while traversing bends and other discontinuities in the pipe.

According to another aspect of the invention, each first section and each second section of the pig is provided with at least three wheels in rolling contact with the pipe, attached for rolling contact with the interior pipe wall, substantially equally spaced around the circumference for centralization of the section within the pipe.

According to another aspect of the invention, a plurality of wheels are attached to each section for rolling contact with the interior surface of a pipe, and each wheel is spring-loaded or otherwise biased outward against the pipe wall with sufficient force greater than the weight of the pig section to facilitate centralization of the pig sections to which the wheels are attached, regardless of the orientation relative to the force of gravity.

According to another aspect of the invention, at least three wheels are equally spaced circumferentially around each section to facilitate centralization of the section, regardless of the rotary orientation of the section within the pipe with respect to the force of gravity.

According to yet another aspect of the invention, each plurality of wheels for each section of the pig includes four or more wheels, spring-loaded in rolling contact with the interior wall surface, to provide additional traction and/or to reduce the load and wear on each individual wheel, thereby facilitating the usefulness of the apparatus as a tractor pig for propelling itself or other devices through a pipe.

According to yet another aspect of the invention, the spiral pig includes at least three sections, with two sections attached for counter-rotation through a middle non-rotating section, with the two counter-rotating sections having a plurality of wheels attached for rolling contact with the pipe surface at equal and opposite angles, and the middle section having a plurality of wheels aligned with the axis of the pipe for holding the central section in non-rotating, linear, axial movement, and further including a synchronized gear mechanism within the middle section to facilitate uniform, equal and opposite rotation of the other two sections. This embodiment advantageously provides a capability for uniform counter-rotational inspection or grid mapping with oppositely angled, overlapping spiral grids along the pipeline.

According to another aspect of the invention, a flexible seal or boot is provided to produce the motive force for moving the pig through the pipeline, driven by flow or differential pressure within the pipeline, and the counter-rotation of the sections results from the angular rolling contact relationship of pluralities of wheels on the counter-rotating sections, which wheels are attached to the sections biased into angled, rolling contact with the interior pipe wall to provide helical motion to the sections.

BRIEF DESCRIPTION OF THE DRAWINGS

The foregoing objects, advantages, and features, as well as other objects and advantages will become more apparent with reference to the description and drawings below, in which like elements represent like numerals and in which:

FIG. 1 is a schematic side view depiction of the counter-rotating pipe inspection device of one embodiment of the present invention within a pipeline section;

FIG. 2 is a graphical depiction of a grid pattern produced by overlapping sensory data from a plurality of flux generator and flux leakage sensors which are counter-rotated through a pipeline;

FIG. 4 is a schematic perspective view of an alternative embodiment of a pipe inspection pig in which each counter-rotating flux generator and sensor section includes a single elongated magnet with a plurality of sensors between north and south poles of flux generating magnets which contact the pipeline; and FIG. 5 is a schematic perspective view of yet another alternative embodiment in which oppositely angled flux fields are created with first and second sets of oppositely angled magnets spaced apart linearly with sensors therebetween to detect anomalies in an overlapping grid pattern.

FIG. 6 is a schematic side view of a spiral tractor pig according to one aspect of the present invention;

FIG. 7 is a partial cut-away view of the spiral tractor pig of FIG. 6, showing one embodiment of the invention with an onboard motor;

FIG. 8 is a side elevation view of a tractor pig, specially adapted for unidirectional lineation through the pipeline;

FIG. 9 is a schematic side elevation of another embodiment of the spiral tractor pig according to one aspect of the invention in which first and second counter-rotating sections are coupled with a non-bending, rotatable coupling mechanism;

FIG. 10 is a partial cut-away section view of the tractor pig of FIG. 9, showing one embodiment of an onboard motor and non-bending, rotational coupling mechanism between the first and second sections;

FIG. 21 schematically depicts an adaptation of a useful spiral tractor pig according to the present invention in which an omni-directional x-ray source may be positioned within a pipeline for providing substantially complete circumferential x-ray film exposure for purposes of circumferential inspection of a pipe, such as at pipeline junctions, welds or the like.

DETAILED DESCRIPTION OF THE PREFERRED EMBODIMENTS

Figure 3:
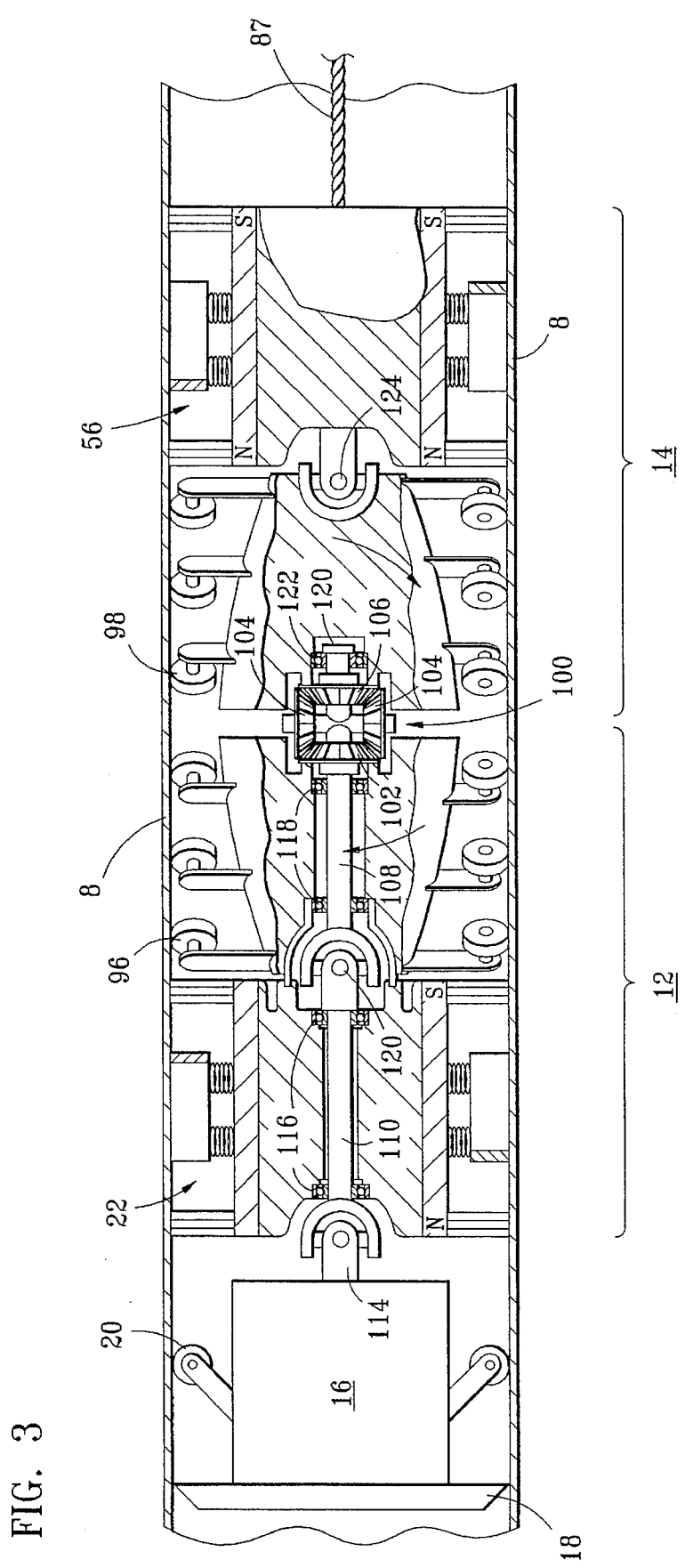
FIG. 3 is a schematic partial cross-sectional view of a magnetic field generator and flux leakage sensor inspection device according to one embodiment of the present invention in which counter-rotating sections are geared for synchronized counter-rotation with each other.

FIG. 1 is a schematic side view depiction of a counter-rotating pipeline inspection device 10 of the current invention. Inspection device 10 comprises a multi-component pig with a first rotating section 12 and a second counter-rotating section 14 which are driven or pulled by a drive section 16 which may be attached to first rotating section 12 and which may be of the type having one or more flexible cups 18 which engage against an inner wall 9 of a pipeline 8 to drive the inspection device 10 therealong with the stream of fluid 7 being carried within the pipeline 8. Typically, the fluid is a natural gas or a liquid hydrocarbon material so that pipeline inspection can be undertaken with minimum interference to the flow of materials being carried within the pipeline. The drive section 16 may also be provided with a mechanical rolling guide 20, which may comprise a plurality of evenly spaced apart rollers 21 spring-loaded against the interior wall 9 of the pipeline so that the flexible cups 18 are maintained in substantially uniform compression therearound. A similar rear guide section (not shown) may also be connected to second rotating section 14 to more accurately support the tracking end of the device 10.

The first section 12 is provided with one or more magnetic flux generator and magnetic sensor units 22. Each of the flux generator and sensor units 22 comprise a magnet 24 having a north pole pipeline contact 26 and a south pole pipeline contact 28 which are fastened to the first section positioned at an angle 30 relative to the central axis 32 of the pipeline 8. The north and south poles are thus spaced apart and produce a substantially uniform magnetic flux field 36 (schematically depicted as an arrow) between the spaced apart north and south poles within the ferromagnetic wall 9 of pipeline 8. Each of the flux generator and sensor units 22 further include a sensor unit 40 corresponding to each of the generator magnets 24 positioned between the north and south pole contacts 26 and 28 and in close proximity of the interior wall 9 of pipeline 8, so that any interruption of the substantially uniform magnetic flux field 36 may be caused by a crack or another anomaly in the ferromagnetic wall 9 of the pipeline 8 at a given location having a component aligned perpendicular to flux field 36 will cause a detectable discontinuity in the flux field which can be detected with sensor unit 40. Each sensor unit 40 may comprise a plurality of individual flux responsive devices 42, such as wire coils, magneto-diodes or Hall effect devices, so that the area between the north and south poles can be further subdivided into identifiable incremental areas. The first section 12 may also include an electronic section 34 by which sensory data from the sensor units 40 is stored, processed, or transmitted to a remote location 38 for storage and/or processing of the data (i.e., a computer at 38). Where the magnetic flux generating units 22 include electromagnets 24, rather than permanent magnets 24, the electronic section 34 may also provide power to the electromagnets 24.

In one preferred embodiment as more fully understood with reference to both FIGS. 1 and 2, the first section 12 rotates at a rate corresponding to the linear movement of pig 10 through the pipeline 8 to produce a helical rotational angle 54 which corresponds to the angle 30 between the north pole contact 26 and the south pole contact 28. Preferably, the angle 30 and the corresponding helical rotational angle 54 are chosen to be approximately 45°. Thus, in this preferred embodiment, the pig moves forward a distance approximately equal to its rotation distance. The helical motion, together with a plurality of circumferentially spaced sensor units 40 and 56 on rotating sections 12 and 14, respectively, allows the pig 10 to move through the pipeline 8, creating a grid pattern of flux and detection paths (as shown in FIG. 2),-at a substantial rate of speed without requiring excessive high rates of rotation of first rotating section 12, which carries the flux generator and sensor units 22.

The second rotating section 14 also has one or more flux generator and sensor units 56, which each have a flux generator magnet 58 having a north pole contact 60 and south pole contact 62 which are positioned at an angle 64 relative to the pipeline axis 32 oppositely directed from angle 30 of the first section. Each of the flux generator and sensor units 56 includes a second flux sensor unit 66, which may include multiple flux sensor devices 68. Thus, the north and south poles 60 and 62 generate a substantially uniform flux field 70 (shown schematically as an arrow) extending between the north and south poles such that the flux field 70 is at an angle 64 with respect to the pipeline axis 32. Anomalies or interruptions with components aligned perpendicular to the flux field 70 will be detected with flux sensor units 66. The second rotating section 14 also includes a second electronic section 74. The first electronic section 34 and the second electronic section 74 may include an onboard plotter at 35, a recorder 75, a processor 76, or a transmitter 78 by which signals or sensory data from the flux sensor units 40 or 66, respectively, may be recorded, processed as with an onboard plotter 35, or transmitted to a remote location 38 with a recorder or processor, such as a computer at 38, at a location aboveground or otherwise remote from the pig. Further, the electronic sections 34 and 74 may provide battery power for operation of the flux generator sensor units. Sufficient electrical power may be provided for a plurality of electromagnets 24 and 58.

Also in the preferred embodiment, as more fully understood, referring to both FIGS. 1 and 2, the second rotating section 14 is rotated at a rate proportional to the longitudinal motion of the pig 10 through the pipeline 8 to produce a helical movement angle 82, which helical angle 82 preferably corresponds to magnet pole position angle 64, which angles 64 and 82 are preferably selected as the opposite of angles 30 and 54 of the first unit. Further preferably, where angles 30 and 54 are positive 45° angles, the angles 64 and 82 are negative 45° angles relative to the axis 32. In order to accommodate the counter-rotation of the two sections 12 and 14, they are rotationally coupled to the drive section 16 with a rotational coupling mechanism 83 and to each other with a rotational coupling mechanism 84. The rotation of the first section 12 is coordinated with the rotation of the second section 14 and their longitudinal separation is maintained substantially constant. Thus, by determining the position of the pig 10, as with an odometer 86 in the drive section 16 or elsewhere, or with a linearly rigid, axially flexible strand 87 (shown in FIG. 3), the length of which is measurable from an originating point, so that a substantially uniform grid pattern of magnetic flux signals or sensory data can be generated by overlapping the signals or sensory data from the first section 12 with the signals or sensory data 40 from the second section. Each of the first flux sensors 40 and each of second flux sensors 66 provide sensory data. Preferably, there are a plurality of flux sensors 40 and flux sensors 66, each with sensory data signals, which sensory data overlaps to produce a grid pattern which can then be indexed to the pipe position at which the signals are generated. Such a pattern may be produced with a continuous onboard plotter 35 or at an above-ground computer 38 receiving the sensory data signals.

FIG. 2 schematically depicts the overlapping paths of travel for a plurality of counter-rotating units 22 and 56. For example purposes, path lines for each of the plurality of first flux generator and sensor units 22a–e produce corresponding path lines 23a–e in FIG. 2 and each of the second flux generator and sensor units 56a–e generate path lines 57a–e. With the path lines only indicated, it will be understood that signals from sensor units 40a–e will be superimposed on path lines 23a–e in FIG. 2 and the signals corresponding to second sensor units 66a–e will be superimposed on path lines 57a–e in FIG. 2. Where the signals from a sensor unit 40 are produced from a series of incremental sensor units 42, those signals will be correspondingly superimposed at appropriate locations at or adjacent to the path lines 23a–e and will be superimposed on either side of the path lines. This will provide a width 92 for path lines 23a–e and a width 94 for path lines 57a–e.

The magnitude of the signal for each incremental area provided from each incremental sensor unit 42 can be superimposed on the signal for each incremental sensor unit 68 as by printing numeric values on a chart indicating a representative sum or by shading the area with a printer, which shading becomes additive corresponding to the strength of the signal, so that higher numbers or darker areas indicate greater discontinuities in the flux where smaller numbers or lighter areas indicate a lesser degree of discontinuity or indicating that the pipe has structural integrity. Large cracks or discontinuities would be indicated by an aligned series of darkened areas or high numbers. It will be understood by those skilled in the art that color coding might also be used as has been done in the past with respect to detecting defects using longitudinal flux line internal devices or from the exterior of a pipeline using somewhat more complex high rotational speed detectors.

In connection with counter-rotating flux generator and sensor units, and particularly with respect to inspecting long lengths of underground pipeline where access to the pig is limited between insert and exit points, the result of the present invention can be maximized by maintaining the counter-rotational sections in accurate synchronization so that they counter-rotate at the same speed and at opposite angles without deviation along the length of the pipeline being inspected. This synchronization is advantageously maintained with the embodiment of the invention as depicted in FIG. 3 in which the front drive unit is provided with axially aligned guide wheels 20 and each counter-rotating section is provided with angularly disposed guide wheels 96 for the first section and guide wheels 98 for the second section. Guide wheels 96 contact the interior surface 9 of pipeline 8 at an angle $\theta = +45°$ relative to axis 32 and guide wheels 98 contact the interior surface of pipeline 8 at an angle $\theta = -45°$ with respect to the axis 32.

In order to properly insure one-for-one counter-rotation in one preferred embodiment as shown in FIG. 3, a mechanical gear mechanism 100 interconnects the first section 12 with the second section 14 such that first section 12 is driven, for example, through engagement of bevel gear 102, with idler bevel gears 104 and the second section 14 is driven by being rigidly connected to bevel gear 106 which engages with idler bevel gears 104. The idler gears 104 are maintained in a fixed position relative to the drive section 16 through shaft 108 which is flexibly coupled to shaft 110 as, for example, through a universal joint 112 and shaft 110 is coupled to drive section 16 through U-joint 114. The first section 12 is mounted on shafts 110 through bearings 116 and also through bearings 118 to shaft 108. This allows the first section 12 to freely rotate relative to the shafts 108 and 110 and relative to the drive section 16. The first section is appropriately guided in a 45° helical rotation with first section guide wheels 96. The second section 14 is rotationally coupled to an end 120 of shaft 108 as through a bearing 122, so that both the first section 12 and the second section 14 are driven linearly along the pipeline 8 by drive section 16. Each section is substantially free to bend relative to the other sections at U-joints 112, 114 and also 124 so that pipelines having a certain amount of curvature can be traversed without binding. U-joint 124 couples the second section angled drive wheels 98 to the second plurality of flux generator and flux sensor units 56. Thus, not only do wheels 96 and wheels 98 cause helical rotation in an amount defined by the respective opposite angles of contact of wheels 96 and 98, but also the relative rotation between first section 12 and second section 14 is precisely maintained through gear mechanism 100. Gear mechanism 100 might be a planetary type gear system, which synchronizes the first section 12 in counter-rotation with the second section 14. Gear mechanism 100 is maintained in a fixed position relative to drive section 16, which drive section 16 is longitudinally aligned along the pipeline by guide wheels 20.

FIG. 4 is another alternative embodiment in which there are elongated magnetic flux generating magnets 126 and 128 with a plurality of sensors 130 and 132 interposed between helically shaped north and south poles 134 and 136 of the first section 12 and 138 and 140 of the second section 14. In this embodiment, a single elongated flux generator may be used in each section to provide complete coverage of the pipeline upon counter-rotation of the first and second sections at opposite 45° angles helically through the pipeline.

FIG. 5 depicts another alternative embodiment of the invention in which first and second counter-directional angular magnetic flux field generators and sensor units 142 and 144, respectively, are provided through a unique positioning of north contact poles 146 and 148 and south contact poles 150 and 152 on first and second flux generating and sensing units 142 and 144, respectively. The first and second units 142 and 144 need not rotate with respect to each other as an angular flux field is created which simply moves along the pipe based upon the appropriate spaced apart orientation of the north and south contact poles of each flux generator. A 45° helical angle exists between the respective north and south contact poles. A plurality of sensors 154 and 156 are positioned interposed between each north and south contact pole along a line corresponding to the helical 45° angle. Thus, a plurality of magnetic flux sensors 154 are evenly spaced and aligned with the predominant flux field generated between the north and south contact poles 146 and 150 of the first section 142. On the second section 146, the contact poles 148 and 152 are oriented in an opposite angular direction, such that if the north poles 146 are forward of the south poles 150 in the first section 142, then the south poles 152 of the second section will be longitudinally aligned with the south poles 150 of the first section 142 and the south poles 150 will be forward of the north poles 148 of the second section. The north poles 148 of the second section 144 will be aligned with the north poles 146 of the first section 142. In this manner, the first and second sections need not be rotated relative to each other, but rather are maintained at precisely the same location and preferably moved straight along the pipeline without any rotation.

In the embodiment described and depicted in FIG. 5, the distance between the sensors which are closest to the south poles is smaller than the distance between corresponding sensors closest to the north poles. The corresponding signals from each of the plurality of sensors can be superimposed one upon the other based upon the rate of travel of the pig and the distance between the corresponding sensors of each section. Thus, coordination of the sensory data for forming an overlapping signal pattern requires that the differences in the distances be appropriately accommodated.

A potential drawback for having fixed position magnets is that the area along the pipe at which the poles contact the pipe surface is not subject to detection with any of the incremental sensors 154 or 156 between the poles. Thus, in another alternative embodiment, two pairs of first and second sections may be used. The first pair would be offset from the second pair a radial distance corresponding to one-half of the circumferential spacing between the north and south poles of each pair. The first and second sections need not be rotated with respect to each other in this alternative embodiment, but rather are maintained in a fixed relationship with respect to each other, so that complete coverage of the internal pipeline surface is accomplished.

FIG. 6 is a side schematic plan view of a tractor pig 160 according to one embodiment of the present invention. A first section 162 and a second section 164 include a first drum 166 and a second drum 168. To the first section, a first plurality of wheels 170(a–h) are attached at first attachment 174 for rolling contact with the inside of the pipe at a first rolling contact angle 176 with respect to the central axis 178 of the drum. Preferably, the plurality of wheels 170 are attached circumferentially around the drum for supporting the first section with its first drum axis 178 substantially coaxially aligned with the central axis of the pipe. A representative construction includes a plurality of attachment mechanisms 194, preferably including a corresponding plurality of pivotable mounting mechanisms 192 (a–h, etc.) and a corresponding plurality of support arms 196 (a–h, etc.) at an angled pivotable relationship to casing 166. The plurality of support arms 196 have corresponding rotational axes 194 (a–h, etc.) which hold wheels 170 (a–h, etc.). The first rolling angle 176 is depicted as the angle between the central axis 178 and the central line 180 of the wheels 170. The particular angle shown is that for wheel 170(b), although the projection angle 176 is preferably the same for all of the first plurality of wheels, so that helical rotation of the first section is characteristic of the movement of the first section through the pipeline. The first plurality of wheels may comprise a central set 170(a–d) and an end set 170(e–h). Each set of wheels is arranged in circumferential alignment, positioned evenly spaced apart from the other wheels of that set. Each set of circumferentially spaced apart wheels is spaced an axial distance from the other to give the section stability. Preferably, the axial distance is the diameter defined by the circumferential wheels. Thus, the section is supported to avoid tumbling within the pipe, which has a diameter smaller than or equal to the circumferential diameter defined by the plurality of wheels. Further, preferably, the axial distance "L" is about one and one-half times the inside pipe diameter "D".

A second plurality of wheels 172 is attached to the second drum 168 of the second section 164. Each of the wheels 172(a–h) of the second plurality of wheels 172 is attached through a plurality of second attachment means 182, so that they each define a second predetermined rolling contact angle 184, as determined by the projection of the axis of the second drum 186 and the center line 190 of wheel 172. Rolling contact angle 184 is the same for each of the plurality of wheels 172(a–h). Rolling contact angle 184 is different from the first predetermined rolling contact angle 176, so that relative rotation between section 162 and 164 results when the pig 160 is moved axially through the pipeline. It has been found and will be understood, based upon this disclosure, that provided angles 176 and 184 are different from each other, and that further provided at least one of the angles 176 or 184 is not aligned with the central axis of the pipe (i.e., not equal to 0 or 180°) and provided that neither angle is 90° with respect to the central axis of the pipe (i.e., not equal to +90° or −90°), relative rotation between section 162 and section 164 will cause the pig to move axially through the pipe, because of the angle of rolling contact. The rate of rotation of either section 162 or 164 will depend upon the relative difference between the angles 176 and 184.

As an example of one preferred embodiment only, if both angles 176 and 184 are equal and opposite at +45° and −45°, substantially as depicted in FIG. 6, then both sections 162 and 164 will rotate with respect to each other at a 1:1 ratio. Both sections 162 and 164 will also rotate equally and oppositely with respect to the pipeline at one-half the rate of relative rotation between the sections 162 and 164.

In another example, if first angle 176 is at a +45° angle, as depicted, and second angle 184 is equal to 0 (i.e., aligned with central axis 186 of the pipe), then, in that event, relative rotation between the sections 162 and 164 will cause the first section 162 to rotate relative to second section 164 at the same rate that first section 162 rotates relative to the pipe. Second section 164, in that example, would not rotate with respect to the pipe, but would merely move axially due to the angular rolling contact of wheels 170 with the pipe.

With reference to FIG. 7, which is a detailed, partial cutaway view of the spiral tractor pig 160 of FIG. 6, details of one preferred embodiment will be further understood. Sections 162 and 164 may be advantageously coupled through a U-joint 200 in rotational relationship with respect to each other. U-joint 200 also permits rotation and bending between the sections through omni-directional pivoting. The rotatable coupling of this embodiment includes a shaft 202 which extends from drum 166 of section 162 and a shaft 204 which extends from drum 168 of section 164. Shaft 202 extends through a bearing 206 for supported coaxial rotation relative to drum 166. In the embodiment shown, shaft 202 also extends through a second support bearing 208. It will be understood that back-to-back U-joints (shown in FIG. 8) can be used at 200 to additionally accommodate short radius bends. The same shafts 202 and 204 would be connected with a double "U" shaft 203.

The motor 210 is rigidly secured as at motor housing 212, pressed against the inside of drum 166. The motor 210 is connected to and receives power from a power supply 214, which power supply 214 may be an electrical cable, a hydraulic hose 214 or a pneumatic hose, connected to an aboveground source of power (not shown), and which power supply cable or hose is connected as at a rotatable coupling 215 to the pig so that it is pulled through the pipe with the pig. Upon receiving power, the motor 210 moves with the drum relative to rotation of shaft 202. Preferably, a switch or valve or other control device, operatively connected and activatable at a position which is remote from the pig-for example, aboveground-to selectively turn the motor on and off or to reverse its direction of rotation. A stepper motor 210 may be used for carefully selected incremental rotation in situations requiring precise positioning of a pig.

Shaft 202 drives shaft 204 through universal joint 200, and shaft 204 is attached directly to drum 168. In the embodiment shown, the attachment is through splines 216 and threaded fastener 218 which tightens against a shoulder 220, thereby holding shaft 204 rigidly within a boss 222 of drum 168. Thus, power supplied through supply 214 to motor 210 causes shaft 202 to rotate relative to drum 166, which rotation of shaft 202 is transmitted through U-joint 200 and shaft 204 into rotation of drum 168. The rotational forces on drum 166 and drum 168 are relatively opposite. Thus, section 162 rotates relative to section 164, and, because of the rolling contact angles 176 and 184 (which are different from each other), relative rotation of the drums causes the pig to move axially through the pipeline in a direction, which depends upon the rolling contact angles and whether the rotation of the motor is counter-clockwise or clockwise. Reversal of the motor direction will cause a reversal of the direction of linear movement through the pipeline. As indicated above, the embodiment of FIGS. 6 and 7 is a bi-directional tractor pig.

FIG. 8 depicts a tractor pig 240 according to another embodiment of the present invention, which is better adapted for movement in a single direction 244 because of the angle 248 of the first plurality of mounting bars 196 on section 162 with respect to the forward axis 178 of the section 162, and angle 249 of the second plurality of mounting bars 242 with respect to forward axis 246 of a modified second section 165, which are both at an obtuse angle, measured from the intended forward direction of the pig through the pipeline. In this embodiment, debris, roots, weld junctions or other obstructions, which may be encountered as the pig traverses through the pipeline, will be likely to push inward on angled mounting bars 196 and 242 and simply cause sufficient compression of springs 198 and 243 to allow the pig to move past any such obstructions. A flexible connection 201 may be constructed with shaft 202, coupled to shaft 204 through a double U-shaft 203. This allows each section to remain centralized even when a short radius bend is traversed by the pig.

FIG. 9 depicts a side plan view of an alternative embodiment of a tractor pig according to the present invention in which a first shortened section 252 is rotatably coupled to a second shortened section 254, with a first plurality of wheels 256 attached to the first section 252 (plurality of wheels 256 a, b, c, etc., are similar in construction to first plurality of wheels 170) and a second plurality of wheels 258 attached to the second section 254 (plurality of wheels 258 a, b, c, etc., are similar in construction to second plurality 172). An axially-rigid, rotatable coupling 260 is provided between section 252 and 254.

FIG. 10 depicts a detailed, partial cutaway schematic view of the tractor pig 250 of FIG. 9, in which the construction of the rigid rotatable coupling 260 and the rotational motor 270 are shown constructed according to one preferred embodiment. Motor 270 is similar in characteristics to motor 210, except that its size may be altered to fit the shorter section, and the shaft construction will be different for non-bending coupling. In this instance, the motor 270 has an elongated shaft 262, which shaft is rotatably supported within a drum extension 266 as with bearing 268 and 272. Motor 270 is preferably affixed within the housing of section 252, and the shaft end 264 is fastened centrally located within a boss 274 of drum section 254. Splines 276, threaded fastener 278 and shoulder 280 can be used for rigid attachment and to ensure that shaft 262 rotates with section 254. Section 252 rotates with the housing of motor 270, so that power to motor 270 causes relative rotation between first and second sections 252 and 254.

According to this embodiment of the invention, the pig 250 is non-bendably at coupling 260, yet it is rotatably attached between first and second sections. Single sets of circumferentially aligned pluralities of wheels 256 and 258, are attached respectively to sections 252 and 254. Thus, both the first and the second sections are stably supported, centrally located with the pipe. The overall length 282 is preferably greater than the overall diameter 284 to prevent tumbling of the pig through the pipe. Preferably, the length 282 is between about 1 and 1½ times the diameter 284. It will be noted that this is substantially the same relationship of the length to the diameter as for each section 162 and 164 of the pig 160 of FIGS. 6 and 7. Thus, the rigid pig 250 is also preferably longer than the diameter of the pipe, and further, preferably, has a length 282 which is about length 1-1½ times the diameter 284 (see FIG. 9), so that the risk of tumbling, tilting and/or jamming of the pig within the pipe is reduced.

Figure 11:
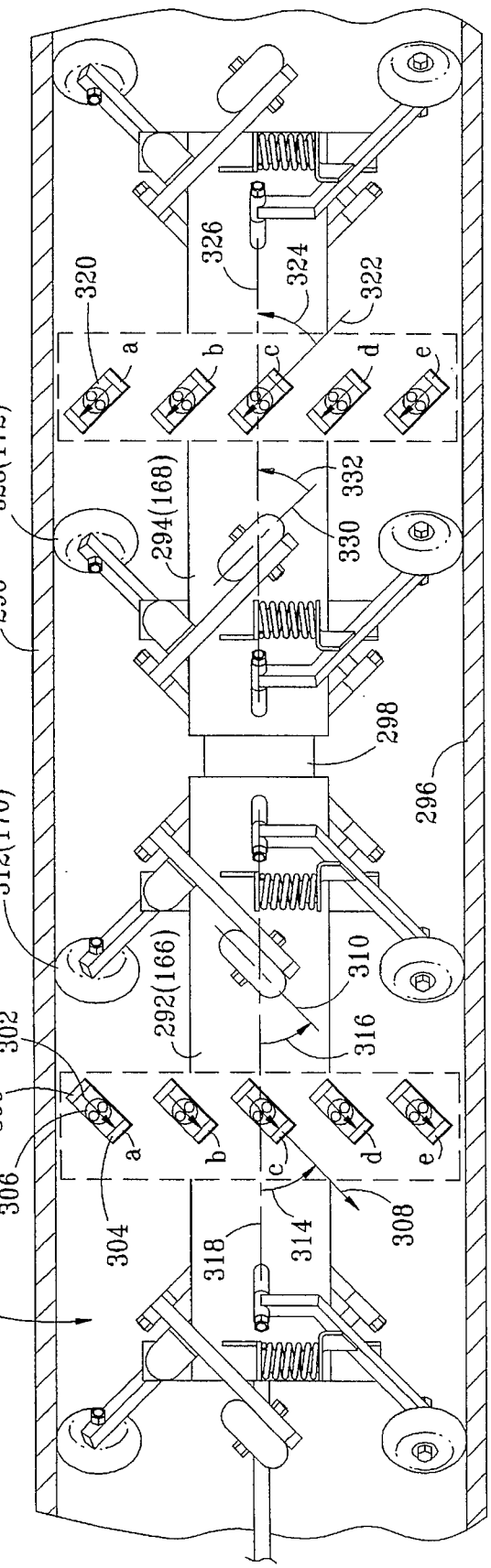
FIG. 11 is a schematic depiction of a useful tractor pig, adapted for magnetic inspection of the interior pipe wall.

FIG. 11 schematically depicts a bi-directional tractor pig 290 with counter-rotating sections 292 and 294, shown schematically inside of a pipe section 296. In this embodiment, the rotatable coupling mechanism 298 is depicted as a non-bendable, rotatable coupling, similar to that as in FIGS. 9 and 10. However, those skilled in the art will understand that coupling mechanism 298 may also be a bendable coupling or a U-joint coupling, similar to coupling 200 as depicted in FIGS. 6 and 7 without departing from some aspects of the present invention. The pig 290 is schematically shown specially adapted for magnetic flux discontinuity detection and for grid pattern pipe inspection. In particular, section 292 is provided with a plurality of magnetic, flux-inducing sensor units 300(*a–e*, etc.), which are schematically representative of sensor units 300, entirely around the circumference of the section, each unit 300 having corresponding north and south poles 302 (*a–e*, etc.) and 304 (*a–e*, etc.) and having a flux sensor 306 positioned therebetween. Each of the sensor units 300 is attached, so that it is rotatable with the drum 292 at a direction 308. Thus, the magnetic flux direction 308 forms an angle 314 with respect to the center line 318 of section 292, which angle 314 is equal to the angle 316 formed between the rolling contact direction 310 and the center line 318 of the plurality of wheels 312.

The counter-rotating section 292 is provided with another plurality of magnetic flux generator and sensor units 320(*a–e*, etc.), each of which is attached for rotation with section 294 and orientated at a direction 322, which forms an angle 324 with respect to center line 326 of section 294. This orientation of the second set of magnetic flux generator and sensor units 320 corresponds to the rolling contact orientation 330 of the second plurality of wheels 328. Rolling contact direction 330 forms an angle 332 with respect to the center line 326, and angle 332 is equal to the angle 324. Both angles 332 and 334 are also equal to, but opposite in direction from, angles 314 and 316. Thus, in one embodiment where the pig is drawn linearly through the pipe, as with a cable or with a fluid pressure rubber boot as in FIG. 12, below, lineation of the tractor pig along the axis of the pipeline causes the first and second sections 292 and 294 to counter-rotate with respect to each other due to the rolling contact with the inside of the pipe 296. Rotation, in turn, causes the magnetic flux units 300 and 320 to spiral in equal but opposite directions through the pipe, thereby providing a grid pattern for detecting anomalies within the pipe. Alternatively, in a preferred embodiment, as depicted in FIG. 11, a rotational power source may be provided onboard either the first section 292 or the second section 294, similar to motor 210 of FIG. 7, or, alternatively, similar to motor 270 of FIG. 10. Relative rotation of the sections by the motor causes the pluralities of wheels 312 and 328 to roll, imparting to the relatively rotating sections both a component of rotation and a component of lineation relative to the pipe 296. Thus, the tractor pig moves linearly through the pipe.

Figure 12:
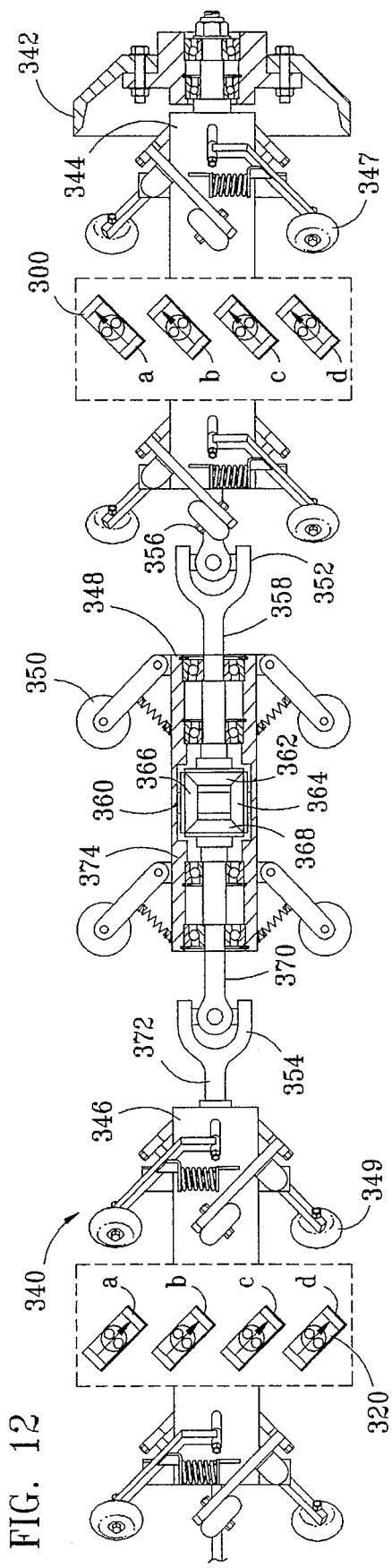
FIG. 12 is an alternative embodiment of a counter-rotating tractor pig, having first, second and middle sections in which the first and second sections are coupled for uniform counter-rotation through the middle section, which middle section is adapted to move axially without rotation, and further depicting a synchronized gear mechanism by which the first and second sections are maintained in substantially constant, uniform counter-rotation.

FIG. 12 depicts another embodiment of a tractor pig 340, which is powered by fluid pressure within the pipeline as with one or more flexible boots or cups 342, each of which may be attached to one of the sections. As shown, boot 342 is attached to a first section 344, although it might be attached to a second section 346 or a middle section 348. In the embodiment shown in FIG. 12, the pig 340 is advantageously designed to move in one direction through the pipe. Each of the sections is coupled for relative rotation to each of the other sections. Further, in the embodiment depicted, the first section is provided with a plurality of sensor units 300(*a–d*, etc.) and the second section 346 is provided with a plurality of sensor units 320(*a–d*, etc.). In this embodiment, the first plurality of wheels 347 and the second plurality of wheels 349 are at equal and opposite of 45° rolling contact angles with respect to the central axis of the pipeline. The middle section 348 has a plurality of wheels 350 aligned for rolling contact parallel to the central axis of the pipeline so that there is a 0 or 180° angular relationship between the rolling contact angle and the central axis of the middle section 348. Section 348, therefore, does not rotate with respect to the pipeline; however, the first section 344 rotates relative to middle section 348 and the second section 346 rotates relative to the middle section 348. Each of the sections is preferably coupled to each other section with U-joint couplings 352 and 354. U-joint 352 includes a first shaft 356 extending from first section 344 and a forward shaft 358 extending from middle section 348. Advantageously, positioned within middle section 348 is a synchronizing gear box 360. In the embodiment shown, synchronizing gear box 360 has a bevel gear 362 attached to forward shaft 358. Idler bevel gears 364 and 366 and an opposite-direction bevel gear 368 are attached to a rearward shaft 370, which couples, through U-joint 354, to a second shaft 372 extending which extends from second section 346. In one embodiment, where first shaft 356 is rigidly attached to section 344 for rotation therewith, as with a spline connection, and where second shaft 372 is similarly directly connected to second section 346 for rotation therewith, linear motion of the pig 340 will result in equal and opposite spiral rotation of first section 344 and second section 346. The resulting equal and opposite rotation will be synchronized not only by the equal angles between a first plurality of wheels 347 and a second plurality of wheels 349, but also will be strictly synchronized through gear box 360.

With reference to FIG. 12, those skilled in the art will also understand that, as an alternative to a boot or plurality of boots 342, power for moving the pig can also be provided by a rotational motor appropriate connected, for example, in middle section 348. In such an embodiment, coaxial, co-rotating and oppositively directed rotational shafts of such a motor would replace either rearward shaft 370 or forward shaft 358. Such motor shafts would be coupled at one rotational shaft to one of the U-joints 352 or 354 and the other rotational shaft coupled to one of the bevel gears 362 or 368. The housing of such a motor (not shown) would be affixed to the casing 374 of middle section 348. In this manner, first section 344 and second section 346 would be driven in equal and opposite directions at an equal and opposite rate, and the non-rotation of middle section 348 would maintain both first and second sections in synchronized orientation within the pipeline, so that a grid pattern of magnetic detection can be accurately mapped throughout the pipeline.

Figure 13:
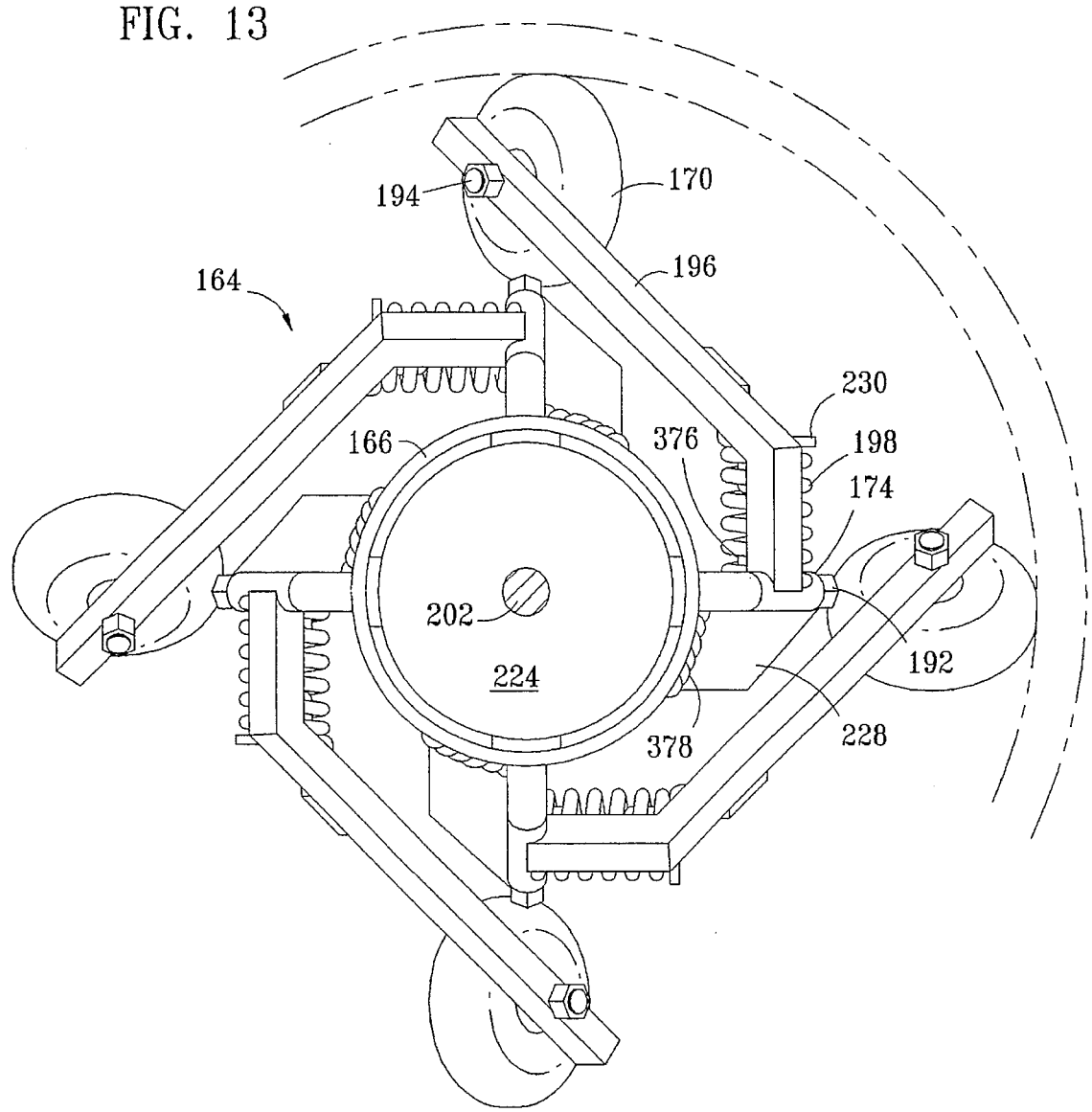
FIG. 13 is a schematic front-end view of one section of a tractor pig according to the present invention, having a plurality of wheels attached for springloaded angular rolling contact with the interior wall of a pipe, and specifically depicting four wheels.

FIG. 13 is a schematic end view of one embodiment of one pig section according to the present invention. For purposes of illustration, the pig section will be designated as "section 166", and the plurality of wheels will be designated as 170*a*, *b*, *c*, *d* and *e*, to correspond with first section 166, as depicted in FIGS. 6 and 7. It will be understood that a similar construction might be typical for any of the foregoing sections or embodiments of pigs according to the present invention. Thus, the construction is representative of the plurality of assemblies or mechanisms 174 for attaching the plurality of wheels 170. Each wheel attachment mechanism 174 preferably includes a pivotable mounting mechanism 192 and a support arm 196 at an angled pivotable relationship with casing 166. At the end of support arm 196, a rotational axis mount 194 holds wheel 170 oriented at a predetermined rolling contact angle with respect to the axis of section 166 and the axis of the pipe. Force is placed outward on each wheel 170 through each spring 198, each of which is mounted to drum 166 as with a welded support fixture 228. A spring attachment device 376 may be attached to bracket 228, which bracket 228 is secured at a weld 378 to drum 166. The opposed spring-tension bracket 230 is attached to support arm 196. The size and compressive force of spring 198 is preferably predetermined so that the radial contact force on each wheel 170 is equal to the radial contact force on each other wheel 170, and, further, the spring force is preferably greater than the weight of the pig section itself, so that the pig section remains substantially centered within the pipeline, regardless of the force of gravity on the pig section.

Figure 14:
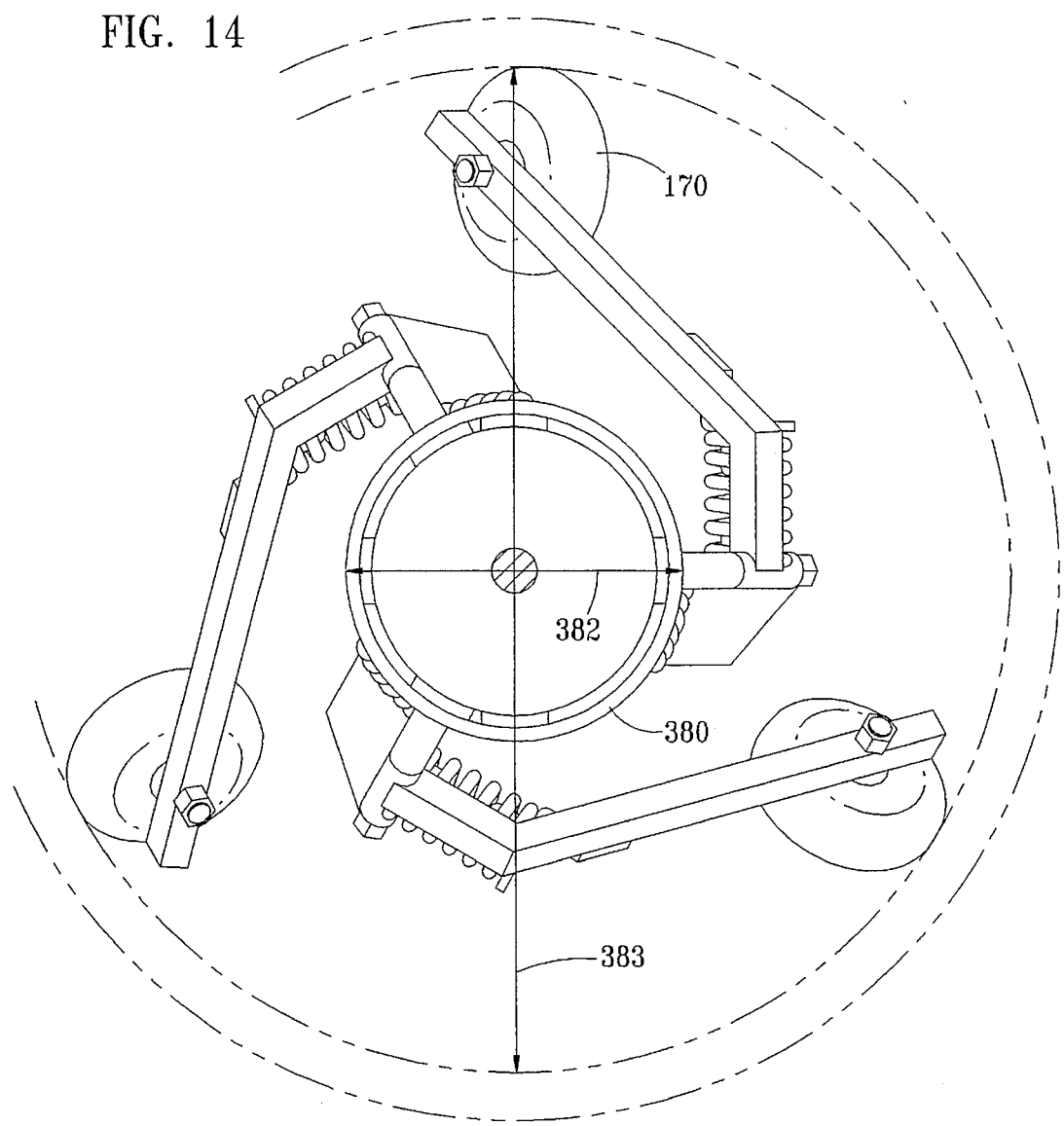
FIG. 14 is a schematic front-end view of one section of an alternative embodiment of a tractor pig according to the present invention, depicting a set of three uniformly-spaced rolling contact wheels.

FIG. 14 depicts an end view of another representative alternative embodiment of a tractor pig according to the present invention in which the plurality of wheels 170 comprises three wheels, attached circumferentially and spaced around the body 380 of a tractor pig, according to this embodiment. Each of three wheels 170 a, b and c is evenly spaced at 120° intervals circumferentially around the pig body 380. An embodiment of a tractor pig 380 with sets of three wheels has the advantage of reduced cost and simplicity over an embodiment as in FIG. 13, with sets of four wheels. In the case of two sets of wheels on each section, there will be six wheels instead of eight wheels. However, the embodiment of FIG. 13, with a larger number of wheels, has the advantage of additional rolling contact and additional traction. Also, additional spring-force support is provided through arms 196 for maintaining the pig centrally located within the pipe. It will be understood by those skilled in the art that more than four support arms 196 and more than four wheels 170 can also be provided for additional traction and for additional centering support. However, it has been found that when the diameter 382 of drum 380 measures about one-half times the inside diameter 383 of the pipe, sets of four wheels, evenly spaced circumferentially around the pig section allows sufficient room for pivotal movement of each of the arms, without contacting the other arms or the other wheels.

Figure 15:
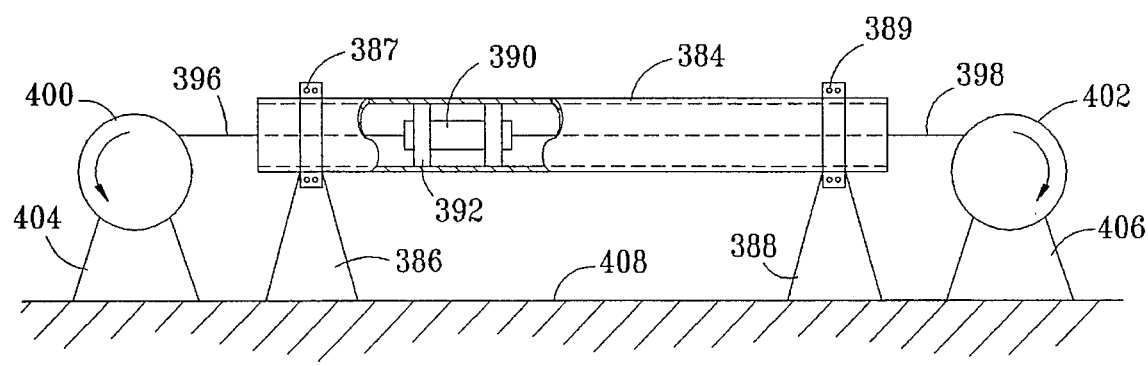
FIG. 15 is a schematic depiction of a prior art wench actuated, pipe-cleaning pig, in which both the winches and the pipe relative to the winches must be securely anchored.

Reference to FIG. 15 shows one prior art use of pigs for cleaning the inside of pipeline and, in particular, illustrates one prior art deficiency in connection with cleaning pipeline sections which are not in service underground or which are not otherwise securely fastened to other fixed structures, as, for example, where a large plurality of old sections of pipe 384 have been removed and are stored on racks aboveground for maintenance, repair and subsequent reuse. In this instance, it will be noted that the pipe 384 is aboveground, as are racks 386 and 388. A cleaning pig 390 of the type having a cleaning brush 392 thereon is pulled by first and second lengths of pull cable 396 and 398, attached between either side of the cleaning pig 390 and opposed first and second winches 400 and 402. In order for such a device to work effectively, both winches 400 and 402 must be securely anchored relative to pipe 384 as to the ground 408 at 404 and 406. Similarly, the pipe 384 must be anchored relative to the winches as through the ground 408. Racks 386 and 388 with clamping devices 387 and 389, securely holding pipe 384, securely fastened to the ground 408. Anchoring, cleaning, releasing, moving and reanchoring the mechanism for cleaning, or for other operations, in each of a plurality of pipe sections 384 stored aboveground can be time-consuming and costly.

Figure 16:
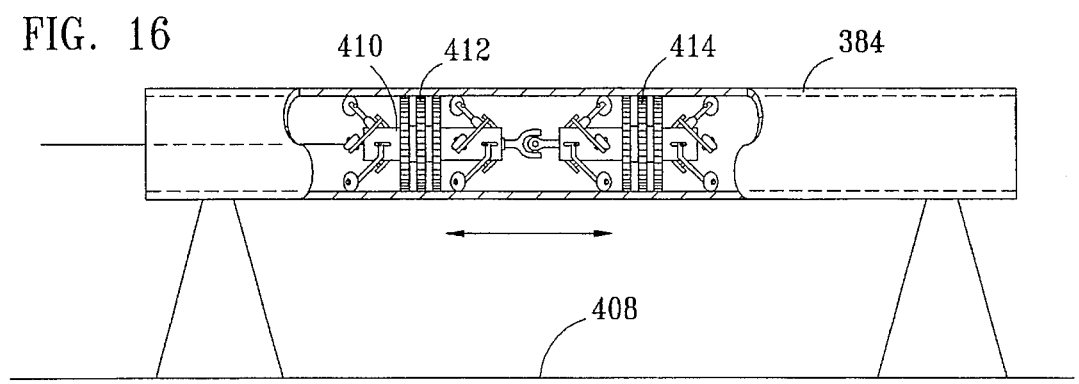
FIG. 16 depicts one embodiment of a tractor pig according to the present invention in which cleaning brushes are attached to the counter-rotating first and second sections, and the pig is self-propelled through the pipe section without requiring either rigid wench anchoring or anchoring of the above-ground pipe to be cleaned.

With reference to FIG. 16, it will be understood that the use of a tractor pig according to the present invention as a cleaning device 410 for aboveground pipe sections 384 advantageously does not require anchoring the pipe section 384, with respect to a winch or the ground 408, for purposes of cleaning. The tractor pig cleaning device 410 is merely provided with its own onboard power source. The power source, such as a motor, causes the pig sections to counter-rotate, and, thereby, the tractor pig 410 draws itself through the pipeline. One or more cleaning brushes 412 are secured to the tractor pig at one or more sections for continuously brushing or otherwise cleaning the entire interior surface of the pipe section 384. It has been found that in most installations, the force of gravity has caused the interior of the pipe to accumulate more debris and foreign matter along one interior side. Usually, the debris-covered side corresponds to a side which at one time was the lower interior surface of the pipe. Further, advantageously, having cleaning brushes 412 and 414, which rotate relative to the pipe, allows each rotating brush 412 and 414 to continuously change the portion thereof, which will be in contact with the interior side wall which is most heavily soiled, sludge-coated or corroded. This will be true, regardless of the orientation of the soiled, sludge-coated or corroded interior side walls. This gives extra cleaning capacity to the brushes before the brushes must be withdrawn and cleaned themselves. The same additional cleaning capacity is also advantageous where the pipe is cleaned while still installed underground or underwater.

Figure 17:
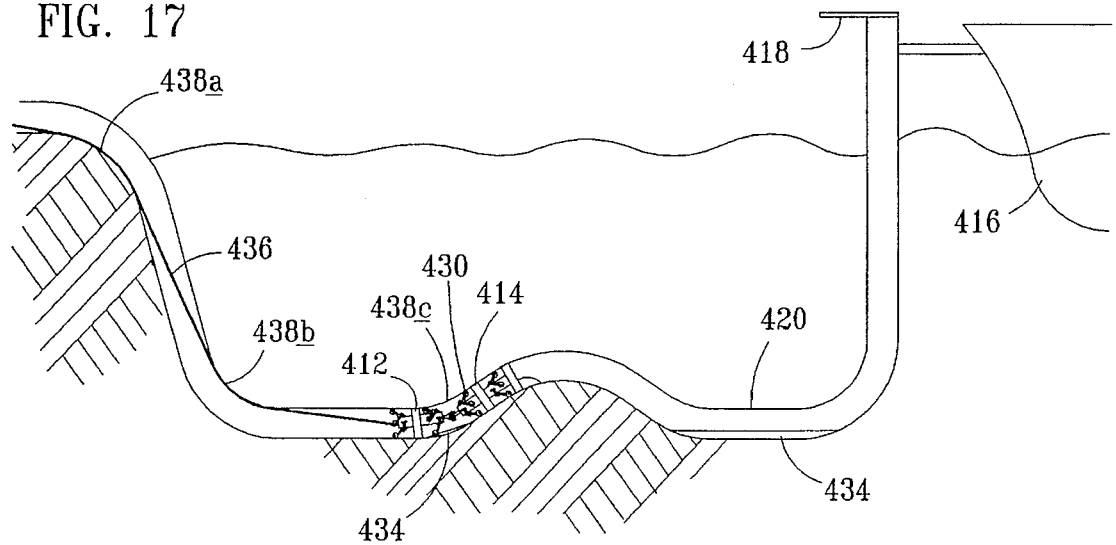
FIG. 17 is a schematic depiction of an improved tractor pig cleaning device in an offshore oil-pumping tanker pipeline situation in which increased traction and full utilization of cleaning brush capacity improves pipe-cleaning effectiveness over the distance traversed by the cleaning pig through the offshore oil-pumping pipeline.

FIG. 17 shows a schematic depiction of an offshore oil tanker 416 and a loading or off-loading platform 418, which is connected with a partially underground and partially underwater pipeline 420, which may periodically require cleaning. As a rule of thumb, for a pig of the type which must drag with it a cable 436 for retraction of the pig if it gets stuck going in, is likely to proceed through the pipeline only until the cumulative total of the bends and curves 438(a–c) in the pipeline add to 180°, and possibly up to about 360°. A pipeline cleaning pig 430 is at risk of becoming stuck, in part due to the frictional drag of the retraction cable 436. The friction at the bends will exceed the force which moves the pig through the pipeline. Prior pigs, of the type with rolling contact, did not always have sufficient traction, especially if there was any slippery sludge buildup 434 in the bottom of the pipe or at the bends in the pipe.

Figure 18:
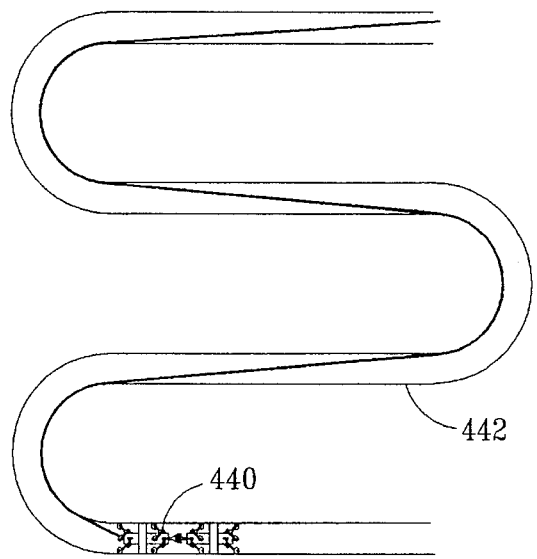
FIG. 18 depicts an embodiment of a spiral tractor pig according to the present invention for traversing a large number of angles in a smaller diameter pipe, such as heat-exchanger coils or other high pressure piping in power-generating plants.

FIG. 18 depicts a smaller version of a tractor pig 440, according to the present invention, in which radiator tubing 442 or heat exchanger coils 442 can be successfully traversed. A pig with the design of the present invention, which is sized for insertion into the small diameter heat transfer pipes 442 can be very useful. For example, in steam generation plants and elsewhere, the cleaning and inspecting of heat transfer coils has become a costly proposition, often requiring complete disassembly of the coil. With the present invention, complete disassembly may be avoided for many cleaning, inspection and repair functions.

Figure 19:
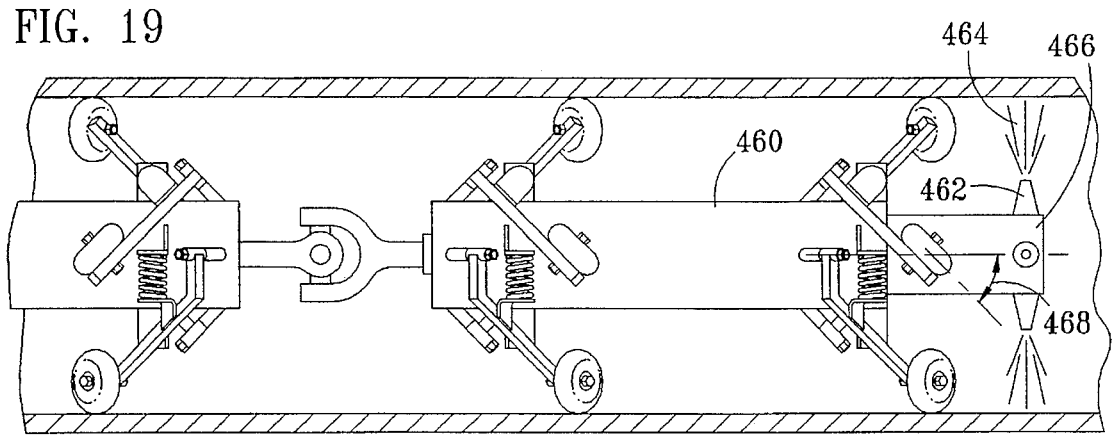
FIG. 19 depicts one embodiment of a useful adaption of a spiral tractor pig according to the present invention in which substantially uniform pipeline spray-cleaning and/or spray-coating may be usefully facilitated.

FIG. 19 is a side plan view of a tractor pig 460 which has been adapted for internal refurbishing of a pipeline, as, for example, with spray coating as with polymeric spray nozzles 462. The rotation of the pig as it lineales through the pipeline, facilitates even deposition of the polymeric coating material 464 through a plurality of spraying nozzles 462. Particularly useful is an embodiment in which a plurality of spray nozzles 462 are evenly spaced around the tractor pig's spray section 466. Further advantageously, the rolling contact angle of the wheels 170 can be constructed and/or adjusted according to the job at hand and the size of the nozzle spray patterns. A larger rolling contact angle 468 increases the number of rotations of a section per unit of lineation. Overlapping deposits of layers of sprayed material can, therefore, be accomplished. Alternatively, reducing the angle 468, with respect to the axis, can cause the pig to move rapidly through the pipeline relative to the number of rotations. Thus, spray nozzles with wide spray patterns can be used to quickly coat a length of pipe.

Figure 20:
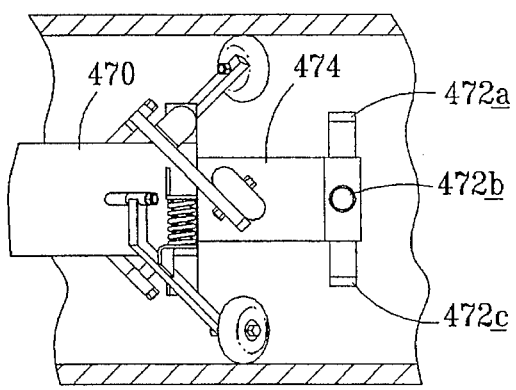
FIG. 20 schematically depicts an adaptation of a spiral tractor pig for carrying visual inspection cameras by which substantially the entire interior wall of a pipeline may be visually inspected.

Referring to FIG. 20, another alternative adaptation of the tractor pig, according to the present invention, includes adaptation of a pig 470 for internal viewing, as through one or more camera lenses 472(a–c, etc.) attached to a camera section 474. The camera image is either recorded onboard or preferably is transmitted to above ground, as along cable 214.

Figure 21:
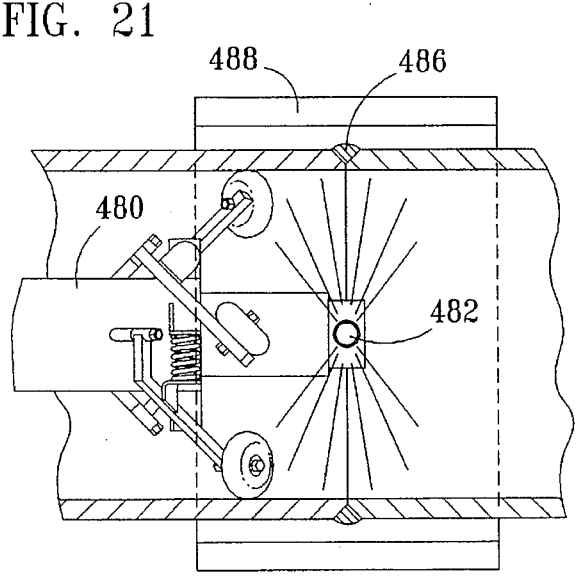

FIG. 21 depicts a use of a tractor pig 480, according to the present invention, for moving a radiation source 482, such as an x-ray radiation source 482, to a position precisely aligned with a portion of the pipeline to be x-ray inspected, For example, a weld joint 486 can be quickly x-rayed. The weld joint 486 can be wrapped entirely with a cylindrical x-ray film plate 488, so that a single activation of the omni-directional radiation source 482 exposes the entire film 488 uniformly from inside the pipeline. Previously, in many cases, the radiation source was positioned outside the pipeline. Thus, a plurality of x-ray plates were used, with multiple external exposures. To get complete exposure, the x-ray source and the plates were repositioned circumferentially relative to the pipeline several times. The present tractor pig can be used to accurately position the omnidirectional x-ray source centrally within the pipeline. One cylindrical x-ray film plate facilitates quick and uniform x-ray exposure by a single source centrally located within the pipeline.

Figure 22:
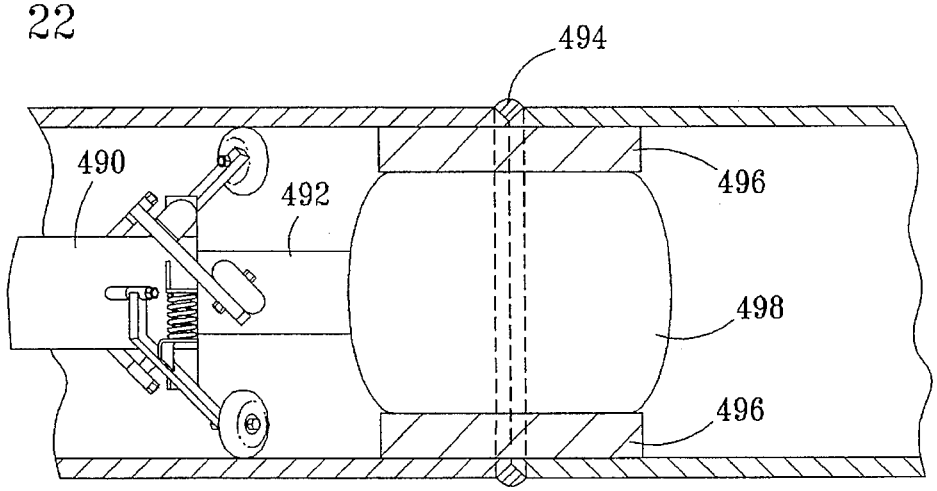
FIG. 22 depicts another embodiment of a useful device attached to a spiral tractor pig according to the present invention by which an inflatable pipe junction clamp may be conveniently positioned and activated for temporarily clamping sections of pipe in position for joint welding.

As shown in FIG. 22, for purposes of forming weld joints, a tractor pig 490 can be used to position a weld clamp 492 at a junction 494 between two sections of pipe. A weld clamp 492 may, for example, include a plurality of alignment bars 496, which may be retracted inward and reversibly expanded outward. In the embodiment shown, a balloon or collapsible bladder 498 is selectably activatable to expand at a weld joint and contract to move to another weld joint. The present invention can successfully position this or other types of clamping mechanisms precisely at joints to be welded. Through activation of the power source and retraction of the clamping bars 492, the tractor pig can be activated to move the clamping device to the next section for joint welding.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A spiral pig apparatus for axial movement through a pipe of the type having a cylindrical interior surface defining a central axis, said spiral pig apparatus comprising:
   (a) a first section;
   (b) a second section, coupled to said first section for axial movement therewith and for relative rotation with respect to said first section;
   (c) a first plurality of wheels attached to said first section, each of said first plurality of wheels attached at a first rolling angle relative to said pipe axis for rolling contact with said interior surface of said pipe and for supporting said first section spaced inward from said interior surface of said pipe;
   (d) a second plurality of wheels attached to said second section, each of said second plurality of wheels attached at a second rolling angle relative to said pipe axis for rolling contact with said interior surface of said pipe, which second rolling angle is different from said first rolling angle of said first set of wheels, and said second plurality of wheels also attached for supporting said second section spaced inward from said interior surface of said pipe; and
   (e) a drive mechanism operatively connected to said spiral pig for causing said pig to move through said pipe as said first and second sections rotate relative to each other.

2. A spiral pig apparatus, as in claim 1, wherein said drive mechanism is operatively connected to said spiral pig for causing said pig to move through said pipe as said first and second sections rotate relative to each other further comprises:
   (a) an onboard motor having a motor housing and a motor shaft for coaxial rotation relative to said housing and which housing is securely affixed coaxially with said first section;
   (b) a power supply operatively connected to said motor and selectively activatable for causing said motor to rotate said motor shaft relative to said motor housing; and
   (c) a coupling mechanism by which second section is coupled to said motor shaft for rotation therewith, so that said first and second sections rotate relative to each other upon rotation of said motor shaft relative to said motor housing.

3. A spiral pig apparatus, as in claim 2, wherein said motor for rotation comprises a hydraulic motor and said power supply comprises a flexible hydraulic supply line which is pulled with said pig through said pipe.

4. A spiral pig apparatus, as in claim 2, wherein said motor comprises an electric motor and said power supply comprises an electrical cable which is pulled with said pig through said pipeline as it moves axially therethrough.

5. A spiral pig apparatus, as in claim 2, wherein said motor comprises pneumatic motor and said power supply comprises an air pressure supply line which is connected to said motor and pulled by said pig through said pipe.

6. A spiral pig apparatus, as in claim 1, wherein said drive mechanism, operatively connected to said spiral pig for causing the pig to move through said pipe as said first and second sections rotate relative to each other further comprises a flexible boot, attached to one of said sections for sliding-seal contact with the interior surface of said pipeline, so that differential pressure, or a fluid flow, within said pipeline causes said boot to move axially through said pipeline, thereby pulling said pig with it and whereby said different rolling contact angles of said first plurality of wheels on said first section, and second plurality of wheels on said second sections, causes said first and second sections to rotate relative to each other.

7. A spiral pig apparatus, as in claim 1, further comprises a nonbendable coupling mechanism by which said first and second sections are interconnected in coaxial alignment and for relative rotation.

8. A spiral pig apparatus, as in claim 1, further comprises a U-joint coupling, coaxially positioned between said first and second sections, by which said first and second sections rotate relative to each other substantially coaxially with each of said first and second sections substantially coaxially aligned with said central axis of said pipe, while a first axis of said first section and a second axis of said section may bend relative to each other at said U-joint couplings therebetween.

9. A spiral pig apparatus, as in claim 1, wherein
   (a) said first plurality of wheels attached to said first section comprises at least three wheels, circumferentially spaced around said first section at uniform angular positions, so that said first section is supported centralized within said pipe; and (b) said second plurality of wheels comprises at least three wheels, circumferentially spaced at substantially even angular positions, so that said second section is supported centralized within said pipe.

10. A spiral pig apparatus, as in claim 1, wherein (a) said first plurality of wheels attached to said first section comprises at least four wheels, circumferentially spaced around said first section at uniform angular positions, so that said first section is supported centralized within said pipe; and (b) said second plurality of wheels comprises at least four wheels, circumferentially spaced at substantially even angular positions, so that said second section is supported centralized within said pipe.

11. A spiral pig apparatus, as in claim 1, further comprising spring-loaded attachment mechanism for providing radially outward bias force on each of the plurality of wheels.

12. A spiral pig apparatus, as in claim 1, wherein said first rolling angle and said second rolling angle are equal but in opposite directions, so that said first and second sections counter-rotate at substantially the same speed with respect to each other as said pig moves axially through said pipeline.

13. A spiral pig apparatus, as in claim 1, wherein one of said first or said second rolling angles is aligned with said central axis of said pipeline, so that said one section with wheels axially aligned in rolling contact with said central axis does not rotate relative to said pipeline as said other section rotates in a spiral action both relative to said pipeline and also rotates relative to said one section.

14. A spiral pig apparatus, as in claim 1, further comprising a middle section, coupled between said first section and said second sections, which middle section has a plurality of wheels aligned with said central axis for rolling contact parallel to said central axis, and each of said first and second sections with synchronized counter-rotation relative to each other.

15. A spiral pig, as in claim 12, wherein said first and second plurality of wheels comprise "at least three wheels" in each plurality, thereby providing rolling traction corresponding to the number of wheels in rolling contact with the interior of the pipeline.

16. A spiral pig apparatus, as in claim 12, wherein said first and second plurality of wheels comprises at least four wheels in each plurality, thereby providing rolling traction corresponding to the number of wheels in rolling contact with the interior of the pipeline.

17. A spiral pig apparatus for axial movement through a pipe of the type having a cylindrical interior surface defining a central axis, said spiral pig apparatus comprising:

(a) a first section having a plurality of wheels attached thereto and spaced circumferentially therearound for rolling contact with said pipe interior, each of said first plurality of wheels positioned at a first predetermined rolling contact angle with respect to said pipe axis;

(b) a second section having a plurality of wheels attached thereto and spaced circumferentially therearound for rolling contact with said pipe, each of said second plurality of wheels positioned at a second predetermined rolling contact angle with respect to said pipe axis and which second predetermined rolling contact angle is different from said first predetermined rolling contact angle; and (c) a drive motor, coupled between said first and second sections for coaxially rotating said first section relative to said second section, so that said angled rolling contact of said first and second plurality of wheels at different relative angles to cause said pig to move axially through said pipe interior.

* * * * *